(12) United States Patent
Dixon et al.

(10) Patent No.: US 11,484,563 B2
(45) Date of Patent: Nov. 1, 2022

(54) COMPOSITIONS AND METHODS FOR ACTIVATING CELLULAR SIGNALING PATHWAYS

(71) Applicant: LifeVantage Corporation, Sandy, UT (US)

(72) Inventors: Brian Dixon, Sandy, UT (US); Christina Beer, Sandy, UT (US); Qiana Martinez, Sandy, UT (US)

(73) Assignee: LIFEVANTAGE CORPORATION, Sandy, UT (US)

( * ) Notice: Subject to any disclaimer, the term of this patent is extended or adjusted under 35 U.S.C. 154(b) by 114 days.

(21) Appl. No.: 17/148,441

(22) Filed: Jan. 13, 2021

(65) Prior Publication Data
US 2021/0213092 A1 Jul. 15, 2021

Related U.S. Application Data

(60) Provisional application No. 62/960,571, filed on Jan. 13, 2020.

(51) Int. Cl.
| | |
|---|---|
| *A61K 36/9066* | (2006.01) |
| *A61K 36/81* | (2006.01) |
| *A61K 36/82* | (2006.01) |
| *A61K 36/53* | (2006.01) |
| *A61K 36/87* | (2006.01) |
| *A61K 36/63* | (2006.01) |
| *A61K 36/31* | (2006.01) |
| *A61K 31/221* | (2006.01) |
| *A61K 31/352* | (2006.01) |
| *A61K 31/385* | (2006.01) |
| *A61K 31/122* | (2006.01) |
| *A61K 31/198* | (2006.01) |
| *A61K 31/165* | (2006.01) |
| *A61K 31/465* | (2006.01) |
| *A61K 33/34* | (2006.01) |
| *A61K 31/05* | (2006.01) |
| *A61K 36/9062* | (2006.01) |
| *A61K 31/353* | (2006.01) |
| *A61K 9/48* | (2006.01) |
| *A61P 39/06* | (2006.01) |
| *A61K 9/20* | (2006.01) |
| *A61K 9/00* | (2006.01) |
| *A61K 36/28* | (2006.01) |
| *A61K 31/455* | (2006.01) |

(Continued)

(52) U.S. Cl.
CPC ........ *A61K 36/9066* (2013.01); *A61K 9/0019* (2013.01); *A61K 9/20* (2013.01); *A61K 9/48* (2013.01); *A61K 31/05* (2013.01); *A61K 31/122* (2013.01); *A61K 31/165* (2013.01); *A61K 31/198* (2013.01); *A61K 31/221* (2013.01); *A61K 31/30* (2013.01); *A61K 31/352* (2013.01); *A61K 31/353* (2013.01); *A61K 31/357* (2013.01); *A61K 31/385* (2013.01); *A61K 31/455* (2013.01); *A61K 31/465* (2013.01); *A61K 31/522* (2013.01); *A61K 33/34* (2013.01); *A61K 36/22* (2013.01); *A61K 36/28* (2013.01); *A61K 36/31* (2013.01); *A61K 36/53* (2013.01); *A61K 36/63* (2013.01); *A61K 36/68* (2013.01); *A61K 36/81* (2013.01); *A61K 36/82* (2013.01); *A61K 36/87* (2013.01); *A61K 36/9062* (2013.01); *A61P 39/06* (2018.01); *A61K 2236/53* (2013.01)

(58) Field of Classification Search
CPC .... A61K 9/0019; A61K 31/357; A61K 33/34; A61K 36/9066; A61K 36/28; A61K 31/05; A61K 9/20; A61K 31/385; A61K 31/30; A61K 31/165; A61K 36/68; A61K 9/48; A61K 31/455; A61K 31/352; A61K 31/198; A61K 31/122; A61K 31/465; A61K 31/522; A61K 36/63; A61K 36/9062; A61K 36/53; A61K 36/82; A61K 31/221; A61K 31/353; A61K 36/22; A61K 36/31; A61K 36/81; A61K 36/87; A61P 39/06
See application file for complete search history.

(56) References Cited

U.S. PATENT DOCUMENTS

| | | |
|---|---|---|
| 7,241,461 B2 | 7/2007 | Myhill et al. |
| 7,384,655 B2 | 6/2008 | Myhill et al. |

(Continued)

FOREIGN PATENT DOCUMENTS

| | | |
|---|---|---|
| WO | 2005/094862 A1 | 10/2005 |
| WO | 2014/111811 A1 | 7/2014 |

(Continued)

OTHER PUBLICATIONS

Hara et al. "Elevation of Cellular NAD Levels by Nicotinic Acid and Involvenment of Nicotinic Acid Phosphoribosyltransferase in Human Cells", Aug. 24, 2007, The Journal of Biological Chemistry vol. 282, No. 34, pp. 24574-24582.

(Continued)

*Primary Examiner* — Aaron J Kosar
(74) *Attorney, Agent, or Firm* — Terrence J. Edwards; TechLaw Ventures, PLLC

(57) ABSTRACT

Compositions and methods for increasing stress response and improving health and slowing the aging process in a user. A composition includes one or more of a first group consisting of milk thistle, ashwagandha, green tea, bacopa monnieri, and turmeric. The composition includes one or more of a second group consisting of acetyl-L-carnitine, quercetin, lipoic acid, coenzyme Q10, cysteine, and grape. The composition includes one or more of a third group consisting of wasabi, theacrine, copper, nicacin, cysteine, and olive extract.

30 Claims, 15 Drawing Sheets

(51) Int. Cl.
*A61K 31/522* (2006.01)
*A61K 36/68* (2006.01)
*A61K 31/30* (2006.01)
*A61K 31/357* (2006.01)
*A61K 36/22* (2006.01)

(56) References Cited

U.S. PATENT DOCUMENTS

| | | |
|---|---|---|
| 7,579,026 B2 | 8/2009 | Myhill et al. |
| 7,923,045 B2 | 4/2011 | Myhill et al. |
| 8,221,805 B2 | 7/2012 | Myhill et al. |
| 8,435,574 B2 | 5/2013 | Myhill et al. |
| 9,265,808 B2 | 2/2016 | McCord et al. |
| 9,289,374 B2 | 3/2016 | Chevreau |
| 9,889,171 B2 | 2/2018 | Chevreau |
| 2013/0309300 A1 | 11/2013 | Lopez Mas et al. |
| 2014/0287071 A1 | 9/2014 | Barnett, III |
| 2014/0308248 A1 | 10/2014 | Giampapa |
| 2014/0348811 A1 | 11/2014 | Nagasawa et al. |
| 2015/0283193 A9 | 10/2015 | McCord et al. |
| 2021/0213086 A1 | 7/2021 | Dixon et al. |
| 2021/0213093 A1 | 7/2021 | Dixon et al. |
| 2021/0213095 A1 | 7/2021 | Dixon et al. |

FOREIGN PATENT DOCUMENTS

| | | |
|---|---|---|
| WO | 2014/151891 A1 | 9/2014 |
| WO | 2015/164504 A1 | 10/2015 |
| WO | 2017200911 A1 | 11/2017 |
| WO | 2021/146344 A1 | 7/2021 |
| WO | 2021146344 A1 | 7/2021 |

OTHER PUBLICATIONS

Wikipedia, "Niacin", Dec. 16, 2019, retrieved on Mar. 17, 2021 from https://en.wikipedia.org/w/index.php?title=Niacin&oldid-931063290.

International Search Report and Written Opinion Received from PCT Application No. PCT/US21/13317, dated Mar. 31, 2021, 11 Pages.

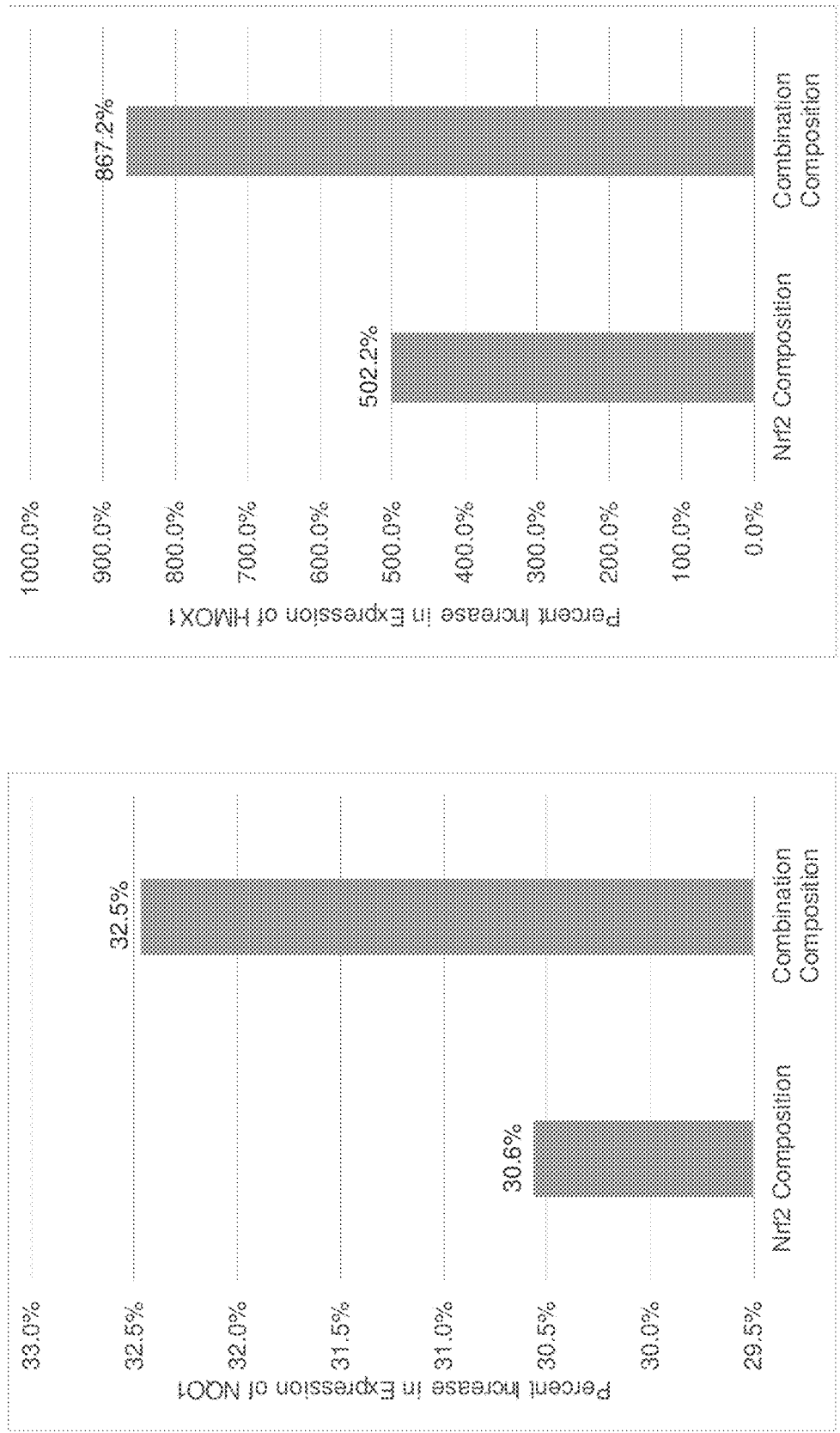

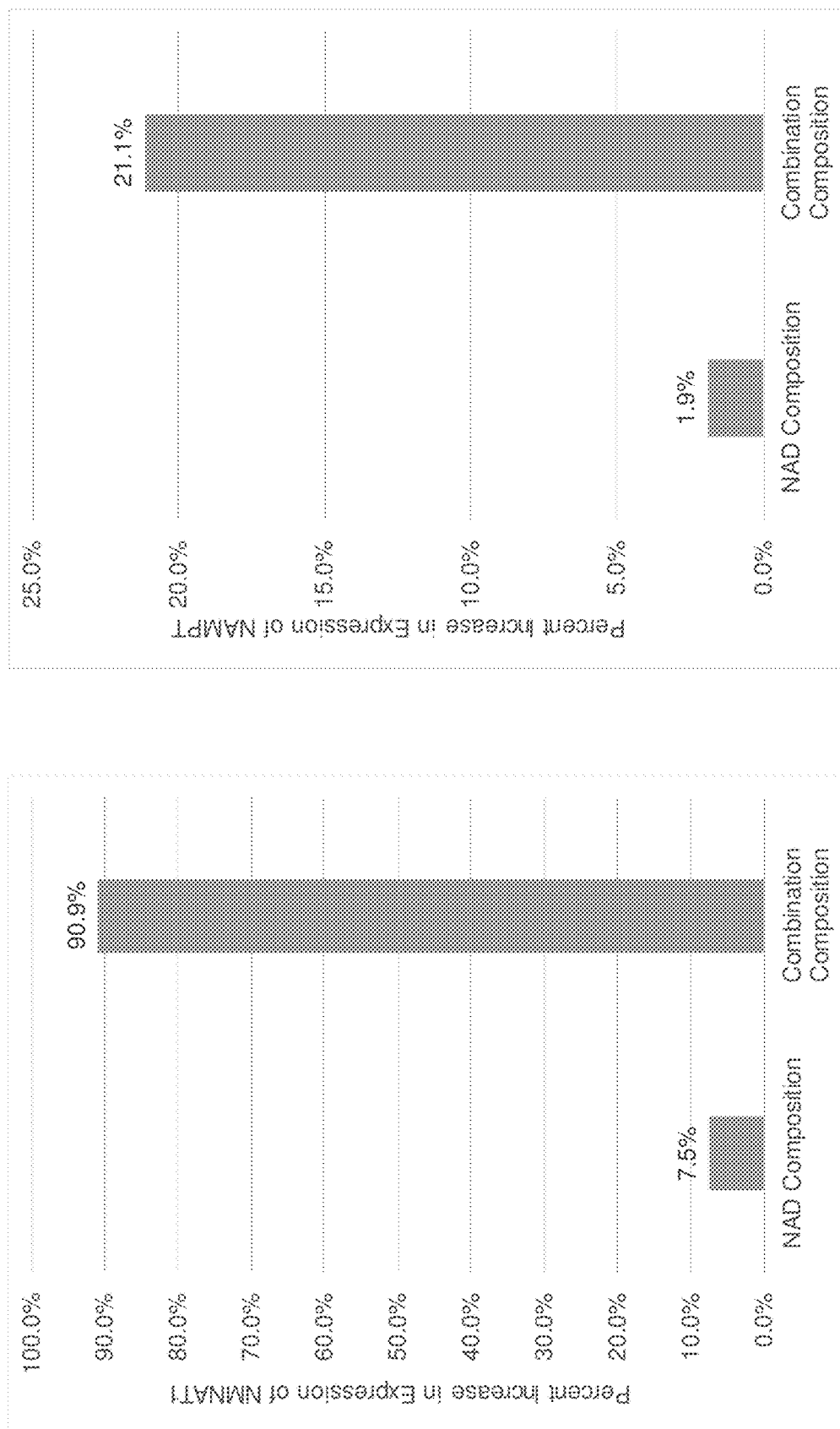

COMPOSITIONS AND METHODS FOR ACTIVATING CELLULAR SIGNALING PATHWAYS

CROSS-REFERENCE TO RELATED APPLICATIONS

This application claims priority to U.S. Provisional Patent Application Ser. No. 62/960,571 filed Jan. 13, 2020 titled "COMPOSITIONS AND METHODS FOR ACTIVATING CELLULAR SIGNALING PATHWAYS," which is incorporated herein by reference in its entirety, including but not limited to those portions that specifically appear hereinafter, the incorporation by reference being made with the following exception: In the event that any portion of the above-referenced application is inconsistent with this application, this application supersedes the above-referenced application.

TECHNICAL FIELD

The disclosure relates generally to compositions of matter and particularly relates to compositions for activating cellular signaling pathways.

BACKGROUND

Stress response is the collection of cellular and physiological changes that occur in response to exposure to a stressor. A stressor can be broadly defined as a chemical, biological, environmental, mental, or other internal or external stimuli with the potential to cause a threat to an organism's homeostasis, well-being, and long-term survival.

Stressors can be direct, indirect, or perceived. Examples of direct stressors include: cold, heat, toxins, biological agents, oxygen deprivation, physical damage/wounds, compromised cellular function, abnormal physiology (e.g., high/low blood pressure, abnormal blood glucose, hormone fluctuations, cholesterol levels, pH, redox status, etc.), exercise, smoking, tobacco, alcohol, drugs, medications, being underweight, being overweight, noise, light, dark, overcrowding, sustained physical or mental exertion, illness, oxidative stress, cellular damage, mutated DNA, and low cellular energy status. Examples of indirect stressors include past traumatic events, major life changes, environmental factors, unpredictable events, workload, social situations, personal/societal beliefs, psychological factors, and financial, divorce, bereavement, unhappiness, and dangerous situations. Examples of perceived stressors include worry or anticipatory stress, fear, lack of control, insecurity, uncertainty, perception, and expectations.

Exposure to any stressor can manifest itself beyond its direct effects. For example, mammals are known to experience headache, fatigue, disturbed sleep, difficulty concentrating, disrupted digestion, and irritability in response to short-term stress. Long-term exposure to stress can lead to depression, high blood pressure, abnormal heartbeat, atherosclerosis, heart disease, heartburn, ulcers, irritable bowel syndrome, upset stomach, cramps, constipation, diarrhea, weight gain or weight loss, altered sex drive, fertility issues, asthma, arthritis, and skin problems such as acne, eczema, psoriasis, and other chronic degenerative diseases.

Because adequately responding to stressors of all types is essential to maintain health, combat disease, and ultimately maintain homeostasis for healthy longevity, organisms have developed extensive networks of biological processes to return to, and maintain, homeostasis. The essential character of these biological processes are conserved evolutionarily from prokaryotes to all eukaryotes including mammals and humans. Collectively, these biological processes are known as an organism's stress response. This stress response can result in the release of hormones, altered physiology, and the activation of so-called "survival genes." The ultimate goal of a stress response is to alleviate the stressor and return the organism to homeostasis.

Cellular signaling pathways are at the core of the body's stress responses. Cells, tissues, and organs are in a constant state of communication. Communication can be facilitated by direct connections via nerves or indirect connections by signaling pathways. Signaling within the cell, or throughout the body, can be carried out by hormones and other signaling molecules that travel the body by way of an intricate network of internal cellular pathways. In some instances, these cellular signaling pathways can be triggered or upregulated by certain compositions and methods. This, in turn, activates the stress response pathways in a user to promote health and slow the effects of aging.

In light of the foregoing, disclosed herein are compositions and methods for activating stress response pathways in a user to promote health and slow the effects of aging.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where:

FIG. 4A is a bar graph illustrating the percent increase in expression of the NQO1 gene three hours after administration of the Nrf2 composition and the combination composition as disclosed herein;

FIG. 4B is a bar graph illustrating the percent increase in expression of the HMOX1 gene three hours after administration of the Nrf2 composition and the combination composition as disclosed herein;

FIG. 6A is a bar graph illustrating the percent increase in expression of the NMNAT1 gene three hours after administration of the NAD composition and the combination composition as disclosed herein;

FIG. 6B is a bar graph illustrating the percent increase in expression of the NAMPT gene three hours after administration of the NAD composition and the combination composition as disclosed herein;

DETAILED DESCRIPTION

Figure 1:
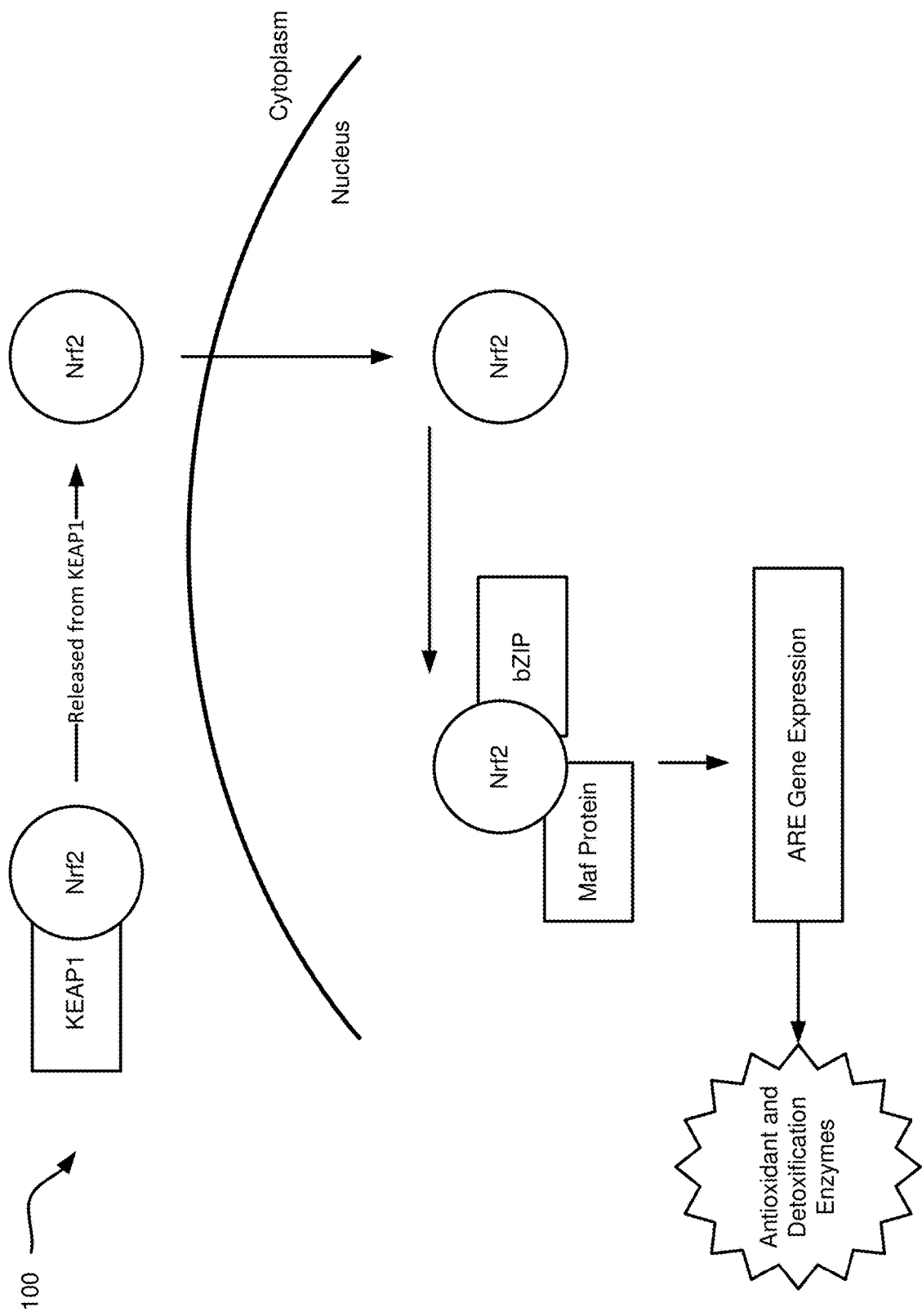
FIG. 1 is a diagram of the Nrf2 pathway for inducing gene expression to generate antioxidants and/or detoxification enzymes.

Disclosed herein are compositions and methods for activating cellular signaling pathways to maintain health and ameliorate the effects of aging. Embodiments of the disclosure are particularly useful for activating the Nrf2 (nuclear factor erythroid 2-related factor 2) pathway, the NRF1 (nuclear factor erythroid 2-related factor 1) pathway, and the NAD (nicotinamide adenine dinucleotide) pathway in a body. These pathways are associated with stress response processes in a body and can be activated to ameliorate the effects of environmental and physiological stressors.

Stress response is the collection of cellular and physiological changes that occur in response to exposure to a stressor. A stressor can be broadly defined as a chemical, biological, environmental, mental, or other internal or external stimuli with the potential to cause a threat to an organism's homeostasis, well-being, and long-term survival.

Stressors can be direct, indirect, or perceived. Examples of direct stressors include: cold, heat, toxins, biological agents, oxygen deprivation, physical damage/wounds, compromised cellular function, abnormal physiology (e.g., high/low blood pressure, abnormal blood glucose, hormone fluctuations, cholesterol levels, pH, redox status, etc.), exercise, smoking, tobacco, alcohol, drugs, medications, being underweight, being overweight, noise, light, dark, overcrowding, sustained physical or mental exertion, illness, oxidative stress, cellular damage, mutated DNA, and low cellular energy status. Examples of indirect stressors include past traumatic events, major life changes, environmental factors, unpredictable events, workload, social situations, personal/societal beliefs, psychological factors, and financial, divorce, bereavement, unhappiness, and dangerous situations. Examples of perceived stressors include worry or anticipatory stress, fear, lack of control, insecurity, uncertainty, perception, and expectations.

Exposure to any stressor can manifest itself beyond its direct effects. For example, mammals are known to experience headache, fatigue, disturbed sleep, difficulty concentrating, disrupted digestion, and irritability in response to short-term stress. Long-term exposure to stress can lead to depression, high blood pressure, abnormal heartbeat, atherosclerosis, heart disease, heartburn, ulcers, irritable bowel syndrome, upset stomach, cramps, constipation, diarrhea, weight gain or weight loss, altered sex drive, fertility issues, asthma, arthritis, and skin problems such as acne, eczema, psoriasis, and other chronic degenerative diseases.

Because adequately responding to stressors of all types is essential to maintain health, combat disease, and ultimately maintain homeostasis for healthy longevity, organisms have developed extensive networks of biological processes to return to, and maintain, homeostasis. The essential character of these biological processes are conserved evolutionarily from prokaryotes to all eukaryotes including mammals and humans. Collectively, these biological processes are known as an organism's stress response. This stress response can result in the release of hormones, altered physiology, and the activation of so-called "survival genes." The ultimate goal of a stress response is to alleviate the stressor and return the organism to homeostasis.

A robust stress response is essential to maintain health, combat disease, and for healthy aging. For many organisms, a loss of stress response and/or the aging process can be a painful and uncomfortable process and may be undesirable. Therefore, there is a desire to effectively maintain a robust stress response through biological, chemical, and nutritional intervention.

Cellular signaling pathways are at the core of the body's stress responses. Cells, tissues, and organs are in a constant state of communication. Communication can be facilitated by direct connections via nerves or indirect connections by signaling pathways. Signaling within the cell, or throughout the body, can be carried out by hormones and other signaling molecules that travel the body by way of an intricate network of internal cellular pathways.

Signaling within a cell begins when a certain signaling molecule comes in contact with a corresponding receptor. To facilitate understanding, the signaling molecule can be analogized to a key and the receptor molecule can be analogized to a lock. The signaling molecule and the receptor molecule may physically pair with one another, and this causes the receptor molecule to be activated. The act of activating the receptor molecule may be analogized to turning the key (the signaling molecule) within the lock (the receptor molecule). An activated receptor molecule begins a chain of signaling events within the cell. The end result of the chain of signaling events is a response to the initial signaling molecule.

One purpose of cellular signaling pathways is to enable a body to respond and adapt to its environment. This adaptive response can happen on a micro scale within a cell. One example of a body adapting to its environment is a body that has hyper activated its detoxification cellular signaling pathways in response to heavy alcohol consumption. A frequent consumer of alcohol can likely consumer greater quantities of alcohol when compared with a person who has never consumed alcohol. This is because the frequent consumer of alcohol has hyper-activated detoxification cellular signaling pathways as a result of continued exposure to alcohol.

There are many cellular signaling pathways that are activated or stalled in response to a cell's environmental conditions. Examples include healing damaged tissues, triggering cells to divide, nerve function, overall metabolism, and triggering the body's immune response to bacteria or viruses. As a result, the body's overall physiology is controlled through cellular signaling pathways on the cellular level.

Cellular signaling pathways begin with activation of a first signaling molecule. The first signaling molecule activates a second signaling molecule after the first signaling molecule is activated by the appropriate receptor molecule. The second signaling molecule then activates the third signaling molecule after the second signaling molecule is activated by the appropriate receptor molecule. This process continues until the final signaling molecule is activated and enters the nucleus of the cell. The nucleus of the cell houses the DNA (deoxyribonucleic acid) of an organism. When the final signaling molecule enters the nucleus, the final signaling molecule can activate or deactivate specific genes within the DNA.

Genes are instructions for the cell to generate a protein or other molecule. For example, genes may instruct a cell to create collagen in furtherance of holding skin together, proteins for shuttling nutrients into the cell, proteins responsible for generating energy, proteins for eliminating toxins, proteins for controlling blood flow, enzymes for defending the cell, and so forth. The cellular signaling pathways that cause proteins and other molecules to be created are essential for the organism's survival. In young and/or otherwise healthy organisms, these cellular signaling pathways work efficiently and correctly and allow for robust adaptation to environmental challenges. As the organism falls out of optimal health and/or ages, these cellular signaling pathways begin to work less efficiently and become less adaptive to environmental changes.

Aging is a complex process driven by diverse changes in genetic, molecular, biochemical, and cellular events in a body. The process of aging is ultimately characterized by a gradual decline in physiological functions. There are currently numerous theories on aging and why aging occurs. Various theories hypothesize that aging occurs due to loss of cellular communication, psychosocial changes, biochemical changes, molecular changes, or loss of cellular function. However, no one theory of aging can account for all changes that are known to occur with age. It is likely that numerous theories on aging are correct. Aging likely progresses due to an additive effect of numerous contributing factors.

One theory of aging encompasses many of the known biochemical, molecular, and cellular theories of aging. This theory is referred to as the "loss of stress response theory." The loss of stress response theory indicates that a young individual can successfully sense and respond to stress more effectively than older counterparts. To date, the loss of stress response theory is the most unifying theory of aging and encompasses many of the changes known to occur in an aging body.

There are many theories on why bodies age. Many of the theories seem unrelated, but one common unifier is the decline in the effectiveness of stress cellular signaling pathways. To date, there are currently three theories of aging that have been the most extensively studied, including the oxidative stress theory of aging, the mitochondrial theory of aging, and the sirtuin theory of aging. While seemingly disjoined, all three of these theories of aging includes a cellular signaling component. As a body ages, the body's cellular signaling pathways fail to react to respective stimuli and signaling responses are attenuated when compared with younger bodies.

Oxidative Stress Theory of Disease and Aging and the Nrf2 Pathway

The oxidative stress theory of aging states that as a body ages, the body accumulates free radicals and other oxidants. If left unchecked, oxidative stress can have serious consequence for the cell. Oxidative stress can ultimately lead to oxidative damage by attacking and damaging essential biological structures in the cell and compromising cellular function.

Antioxidants are the cell's primary defense against free radicals and other oxidants. There are two major classes of antioxidants, including: dietary antioxidants obtained through food and nutritional supplements; and endogenous antioxidants produced by the body. However, in rigorous trials of antioxidant supplements in large numbers of people have not found that high doses of antioxidant supplements prevent disease.

Endogenous antioxidants are created by the body and serve as the primary line of defense against oxidative stress. In general, endogenous antioxidants prevent free radicals and oxidants from being formed or remove free radicals and oxidants from the body. Endogenous antioxidants form a complex network of antioxidant metabolites and enzymes. These networks work together through the cell to neutralize free radicals and oxidants and protect important biological structures from oxidative damage. While most dietary antioxidants can only be used once, endogenous antioxidants can neutralize numerous oxidants because they are constantly regenerated back to their "active" or reduced state. This can be accomplished by a redox cycle occurring within the cell.

Endogenous antioxidants can be upregulated in times of increasing oxidative stress. The primary transcription factor responsible for upregulating endogenous antioxidant and detoxification pathways is Nrf2. Nrf2 is known as the nuclear factor erythroid 2-related factor 2 or alternatively as the nuclear factor erythroid-derived 2-like 2. Nrf2 is a transcription factor that in humans is encoded by the NFE2L2 gene. Nrf2 is a basic leucine zipper (bZIP) protein that regulates the expression of antioxidant proteins that protect against oxidative damage triggered by injury and inflammation. The Nrf2 cellular signaling pathway triggers activation of Nrf2 and thereby triggers the generation of endogenous antioxidant and detoxification pathways. Under times of normal or low oxidative stress, Nrf2 is normally found anchored to another protein in the cell membrane called KEAP1 (Kelch-like ECH-associated protein 1). During times of oxidative stress, oxidants, and other electrophiles release Nrf2 from KEAP1. Nrf2 then translocates to the nucleus of the cell where it binds a promoter sequence to ultimately activate target antioxidant and detoxification genes. As a body ages, the activity of the Nrf2 cellular signaling pathway decreases in its ability to sense oxidative and toxicological threats and ultimately upregulate the target genes.

Mitochondrial Theory of Disease and Aging and the NRF1 Pathway

Another major theory of aging is the mitochondrial theory of aging. Mitochondria are essential for cellular function. It is estimated that about 95% of the energy a body needs to function is produced by mitochondria. The mitochondria generate energy by breaking down food and capturing high-energy electrons in the process. When mitochondria are functioning properly, they harness the energy of these electrons to produce energy for the cell. At the end of this process, the mitochondria attach these electrons to molecular oxygen that is ultimately detoxified to water. However, this process is not completely efficient. Even in a young body with healthy mitochondria, electrons can escape this process and potentially form free radicals and other oxidants.

The mitochondrial theory of aging states that as a body ages, the mitochondria work less efficiently. As the mitochondria age they do not produce as much energy and release more stray electrons that can create more free radicals and other oxidants. The reduction in energy production comprises cellular function. The increase in free radicals and other oxidants can damage cell structures including the mitochondria. The mitochondrial damage continues to further comprise mitochondrial function and leads to a vicious downward spiral of even less mitochondrial efficiency and the generation of more free radicals and oxidants. This ultimately contributes to an increase in the overall cellular burden of oxidative stress.

Numerous nutrients are known to support mitochondrial health. Example nutrients include lipoic acid, acetyl-L-carnitine, and coenzyme Q10. Lipoic acid is fat and water soluble and has 400 times the antioxidant power of vitamin E and vitamin C combined. Lipoic acid is shown to neutralize oxidants that damage mitochondria, recycle other antioxidants, and regenerate glutathione. Acetyl-L-carnitine is an amino acid naturally produced in the body that assists in generating energy. Coenzyme Q10 is a fat-soluble antioxidant concentrated in the mitochondria. Coenzyme Q10 is involved in shuttling electrons through the electron transport chain of the mitochondria to ultimately produce energy.

A major cellular signaling pathway involved in mitochondrial health is NRF1. NRF1 is known as nuclear factor erythroid 2-related factor 1. The NRF1 cellular signaling pathway directly and indirectly regulates a number of genes involved in mitochondrial health, turnover, and biogenesis. These include another protein named Nrf1 (nuclear respiratory factor-1). Nrf1 activates the expression of key genes involved in metabolism, cellular growth, energy production, and mitochondrial DNA transcription and replication. Together with Nrf2, NRF1 performs the function of coordination gene expression between nuclear and mitochondrial genomes. An additional protein shown to support mitochondrial health is PGC1-alpha (peroxisome proliferator-activated receptor gamma coactivator-1-alpha). PGC1-alpha is a transcriptional coactivator that regulates genes involved in energy metabolism. PGC1-alpha is the key regulator of mitochondrial biogenesis, mitochondrial turnover, blood pressure, and cholesterol levels.

Sirtuin Theory of Disease and Aging and the NAD Pathway

Another major theory of aging is the sirtuin theory of aging. The sirtuin theory of aging was born of studies examining the health benefits of caloric restriction. Caloric restriction is the process of restricting caloric intake by as much as 40-60 percent. In numerous experimental models, animals with a calorically restricted diet experience significant increases in maximum lifespan by as much as 60 percent. Based on these studies, it was ultimately determined that a family of proteins referred to as the "sirtuins" were required to experience the increase in lifespan brought on by caloric restriction. Numerous health benefits are associated with caloric restriction. Humans undergoing caloric restriction experience improvements in risk factors for diabetes and cardiovascular disease, lower blood pressure, lower cholesterol, weight loss, increased sexual function, better sleep, improved cognitive function, increased autophagy, and a healthy inflammatory response.

The enzymatic activity for many sirtuin proteins requires the molecule $NAD^+$. NAD is nicotinamide adenine dinucleotide and is a cofactor that is central to metabolism. NAD exists in the cell as a redox couple where $NAD^+$ is the oxidized molecule while NADH is the reduced molecule. The $NAD^+$/NADH ratio is important for controlling a number of cellular signaling pathways. Under normal conditions, the cell tightly regulates the $NAD^+$/NADH ratio. However, changes in metabolism like long-term or short-term caloric restriction can change this ratio. Several key enzymes, including sirtuins, are activated by an increase in $NAD^+$ caused by a change to the $NAD^+$/NADH ratio.

$NAD^+$ is created in two pathways through the $NAD^+$ biosynthetic pathway, including the de novo pathway and the salvage pathway. In humans, de novo synthesis of NAD involves the amino acid tryptophan. Quinolinic acid is generated directly from tryptophan. The quinolinic acid is converted to nicotinic acid mononucleotide (NaMN) by transfer of a phosphoribosyl moiety. An adenylate moiety is transferred to form nicotinic acid adenine dinucleotide (NaAD). The nicotinic acid moiety in NaAD is amidated to nicotinamide (Nam) and ultimately forms nicotinamide adenine dinucleotide ($NAD^+$).

The salvage pathway in humans involves recycling individual components of $NAD^+$ containing a pyridine base. The three vitamin precursors used in these salvage metabolic pathways are nicotinic acid (NA), nicotinamide (Nam), and nicotinamide riboside (NR). These compounds can be taken up from the diet or produced within cells by digestion of cellular $NAD^+$ and are termed vitamin B3 (niacin) or NR. These precursors can take up extracellular $NAD^+$ from their surroundings. Nicotinamide and nicotinamide riboside can be absorbed from the gut.

The salvage pathway reactions are essential in humans despite the presence of the de novo pathway. The high requirement for $NAD^+$ results from the constant consumption of the $NAD^+$ in reactions such as posttranslational modifications, including those by sirtuins. Thus, the salvage pathway is the most important for biological function.

Nutrigenomics

Nutrigenomics is the study of how foods and individual nutrients can affect gene expression and how genes can affect how the body metabolizes food. Nutrigenomics demonstrates that certain nutrients can activate cellular signaling pathways. Disclosed herein are means for engaging cellular signaling and biochemical pathways to unlock specific health mechanisms in cells, tissues, and organs. Specifically, by leveraging cellular signaling and biochemical stress response pathways known to be implicated in the aging process, the compositions and methods disclosed herein to reduce oxidative stress, optimize mitochondrial function, and activate the sirtuin family of proteins.

An embodiment of the disclosure is a composition designed to activate the Nrf2 protein irrespective of the cell's environment. The activated Nrf2 enters the nucleus of the cell and activates certain genes to raise the cell to a heightened state of readiness for neutralizing free radicals and other oxidants and activate detoxification pathways. The composition therefore reawakens Nrf2 and activates Nrf2 to its full potential to activate stress response pathways and to slow the rate of aging.

An embodiment of the disclosure is a composition for improving mitochondrial health by activating the NRF1 pathway. NRF1 is responsible for mitochondrial health and turnover. Poorly performing and decayed mitochondria should be removed and replaced with new, efficient mitochondria. NRF1 has been shown to remove damaged mitochondria and prompt the generation of new mitochondria within the cell. NRF1 additionally helps coordinate gene function between mitochondria and the nucleus. The composition targets the NRF1 protein and delivers nutrients for improving mitochondrial health.

An embodiment of the disclosure is a composition that targets cellular signaling pathways involved in the salvage pathway for $NAD^+$. The composition upregulates genes involved in the $NAD^+$ biosynthetic pathway. The composition nutrigenomically targets the appropriate genes to increase levels of $NAD^+$ and thereby increase sirtuin activity.

In the following description of the disclosure, reference is made to the accompanying drawings, which form a part hereof, and in which is shown by way of illustration specific implementations in which the disclosure may be practiced. It is understood that other implementations may be utilized, and structural changes may be made without departing from the scope of the disclosure.

Before the structures, systems, methods, and compositions for activating cellular stress signaling pathways are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified ingredients, materials, or steps and those that do not materially affect the basic and novel characteristic or characteristics of the claimed disclosure.

As used herein, "effective amount" means an amount of an ingredient or a component of the product that is nontoxic, but sufficient to provide the desired effect and performance at a reasonable benefit/risk ratio attending any dietary supplement or product. For example, an effective amount of a vitamin or mineral is an amount sufficient to prevent a deficiency thereof and to reduce the incidence of some adverse effects.

As used herein, a component or ingredient of a composition may include any suitable form of the component or ingredient, such as, for example, an extract, a powder, a tincture, an absolute, an essential oil, a paste, a dehydrated form, and so forth. It should be appreciated that any suitable form or combination of a component or ingredient may be used unless otherwise specified.

As used herein, an extract includes any substance obtained from a raw material. An extract may be obtained from a blossom, fruit, root, whole plant, leaf, or other component of an agricultural or horticultural component. An extraction may be obtained through expression, absorption, maceration, distillation, grinding, dehydration, and so forth. An extract may be stored in a solvent such as ethanol or water or may be stored in a dry form such as a powder.

Unless defined otherwise, all technical and scientific terms used herein have the same meanings as commonly understood by one of ordinary skill in the art to which this disclosure pertains and belongs.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates an Nrf2 pathway 100 for prompting the creation of antioxidants and detoxification enzymes. The Nrf2 pathway 100 illustrated in FIG. 1 can prompt a body to generate enzymes for reducing levels of free radicals, other oxidants, and toxins. Free radicals are atoms, molecules, or ions that include an unpaired valence electron. Free radicals are highly chemically reactive and can damage cells, causing illness and aging. Oxidants are reactants that oxidize or remove electrons from other reactants during a redox reaction. Free radicals, other oxidants, and toxins are believed to contribute to disease, cancer, and the process of aging. The body is capable of creating antioxidants and detoxification enzymes for neutralizing and removing free radicals, other oxidants, and toxins. In some instances, it is beneficial to prompt the generation of additional antioxidants. The Nrf2 pathway 100 is associated with prompting the generation of additional antioxidants.

Nrf2 controls the basal and induced expression of an array of antioxidant response element-dependent genes to regulate the physiological and pathophysiological outcomes of oxidant exposure. Nrf2 is linked to reducing oxidative stress and toxicity and regulating antioxidant defense by the body. Reactive oxygen and nitrogen species are constantly generated in the body from internal metabolism and external exposure. In normal cells, reactive oxidants are produced in a controlled manner and serve some useful purposes. Oxidants formed in response to physiological cues act as important signaling molecules to regulate processes such as cell division, inflammation, immune function, autophagy, and stress response. However, uncontrolled production of oxidants results in oxidative stress that impairs cellular functions and contributes to the development of chronic disease, toxicity, and aging.

Nrf2 is the primary transcription factor responsible for upregulating endogenous antioxidant and detoxification pathways. In humans, Nrf2 is encoded by the NFE2L2 gene. As illustrated in FIG. 1, Nrf2 is normally found anchored to another protein outside the nucleus called KEAP1. As illustrated, Nrf2 can be released from KEAP1 such that it can pass the wall of the nucleus and translocate to the nucleus. Once in the nucleus, the Nrf2 binds a promotor sequence to ultimately activate a target antioxidant gene and prompt the gene to create antioxidants and detoxification enzymes. In FIG. 1, the Nrf2 is bound to an antioxidant responsive element (ARE) and a basic leucine zipper domain (bZIP). The combination of the Nrf2, the antioxidant responsive element, and the basic leucine zipper domain causes a gene to express and prompts the generation of antioxidants and detoxification enzymes.

The Nrf2-ARE activation is a stress response pathway that confers resistance to a variety of oxidative, stress-related, and neurodegenerative insults. ARE is a regulatory element or enhancer sequence that is found in the promoter region of several genes encoding detoxification enzymes and cytoprotective proteins. The core sequence of ARE includes 5'-TGACNNNGC-3'. ARE binds with Nrf2 in the nucleus of the cell to transcriptionally activate antioxidant genes.

The basic leucine zipper domain (bZIP domain) is found in DNA binding eukaryotic proteins. One part of the bZIP domain includes a region that mediates sequence-specific DNA binding properties to the ARE. The DNA binding region comprises a number of basic amino acids such as arginine and lysine. bZIP transcription factors are found in eukaryotes and form one of the largest families of dimerizing transcription factors.

Disclosed herein are compositions and methods for activating the Nrf2 pathway 100 and thereby causing antioxidants and detoxification enzymes to be generated by a body. Therefore, the compositions and methods disclosed herein are effective for neutralizing free radicals and reducing oxidative stress, toxicological burden that can damage cells, tissues, and organs.

An embodiment of the disclosure is a composition for activating the Nrf2 pathway. This composition is referred to herein as the Nrf2 composition. The Nrf2 composition may include one or more of calcium, silybum marianum extract, bacopa monnier whole herb extract, *Camellia sinensis* leaf extract, magnesium, silica, medium chain triglycerides purified water, opadryl II clear, silicon dioxide, stearic acid, calcium phosphate, hydroxypropyl methylcellulose, oxidizable diphenols, phenylenediamines, quinones, Michael reaction acceptors, isothiocyanates, sulfoxylthiocarbamates, thiocarbamates, dethiolethiones, polyenes, hydroperoxides, trivalent arsenicals, heavy metals, dimercaptans, curcuma longo extract, proanthocyanins, resveratrol, garlic extracts, cinnamon extracts, ferulic acid, rhubarb extract, ginger extracts, ginseng extracts, skullcap extracts, Brazilian green propolis, or myricetin.

Figure 2:
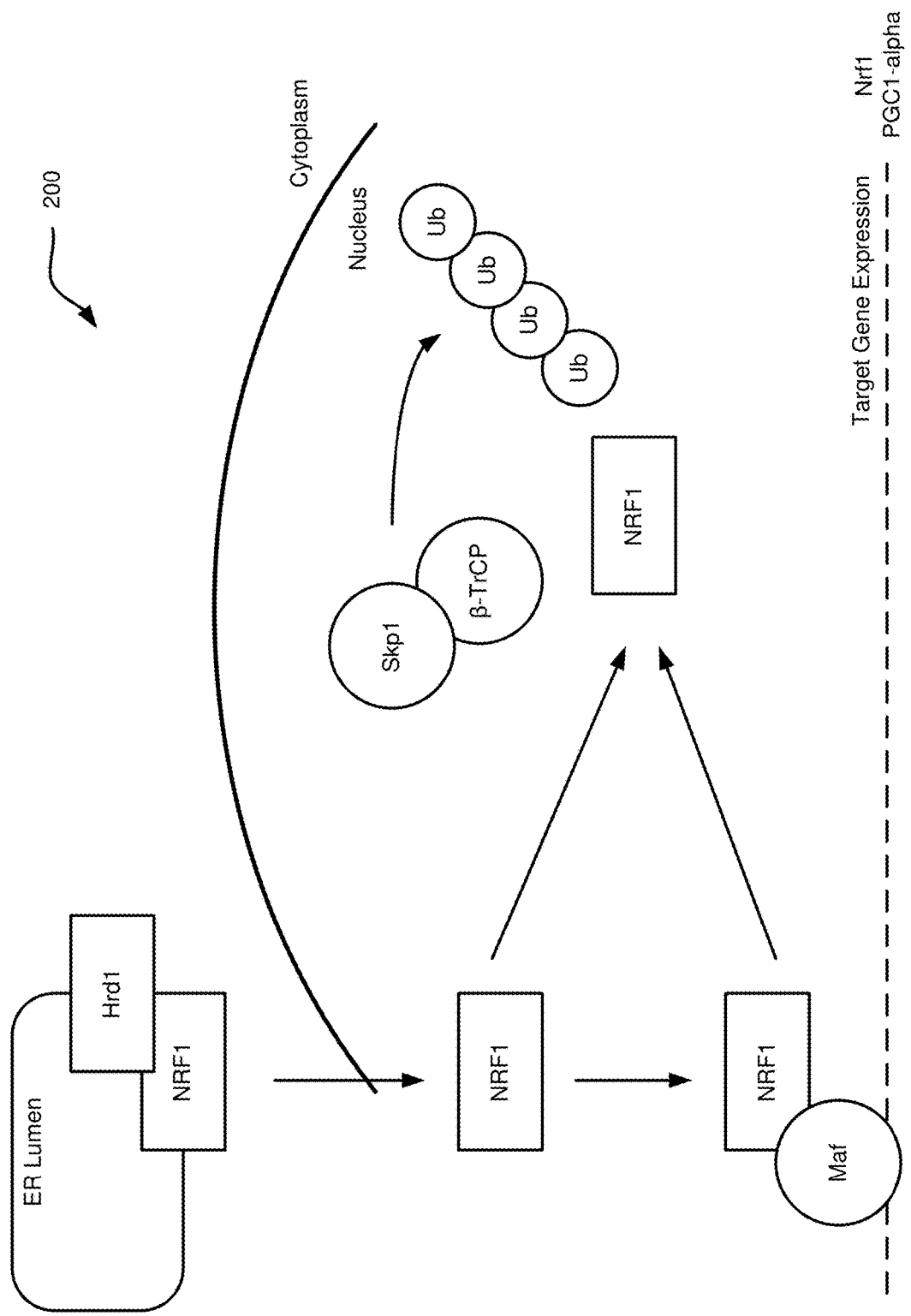
FIG. 2 is a diagram of the NRF1 pathway for inducing gene expression of the Nrf1 gene and/or the PGC1 gene to regulate metabolic activity.

FIG. 2 illustrates an exemplary NRF1 pathway 200. NRF1 functions as a transcription factor that activates the expression of some metabolic genes for regulating cellular growth and nuclear genes required for mitochondrial respiration. NRF1 and Nrf2 can work together to mediate coordination between nuclear and mitochondrial genomes by regulating the expression of nuclear-encoded proteins.

As illustrated in FIG. 2, NRF1 is normally tethered to Hrd1 in the lumen of the endoplasmic reticulum (ER). Hrd1 is a ubiquitin ligase complex that mediates the degradation of misfolded endoplasmic reticulum proteins. NRF1 can be untethered from Hrd1 and pass the nucleus membrane to translocate to the nucleus. In the nucleus, NRF1 can bond with small Maf proteins. Small Maf proteins are leucine zipper proteins associated with repressing and activating transcription of genes. Further in the nucleus, β-TrCP serves as an adaptor for the Skp1 protein ubiquitin ligase and promotes the degradation of NRF1 by catalyzing its polyubiquitination. This augments the expression of NRF1 target genes.

An embodiment of the disclosure is a composition for activating the NRF1 pathway. This composition is referred to herein as the NRF1 composition. The NRF1 composition may include one or more of L-carnitine, quercetin, coenzyme Q10, onion bulb extract, grape extract, fruit extracts, ubiquinol, quercetin, magnesium, proanthocyanins, cocoa extracts, or ginseng extracts.

Figure 3:
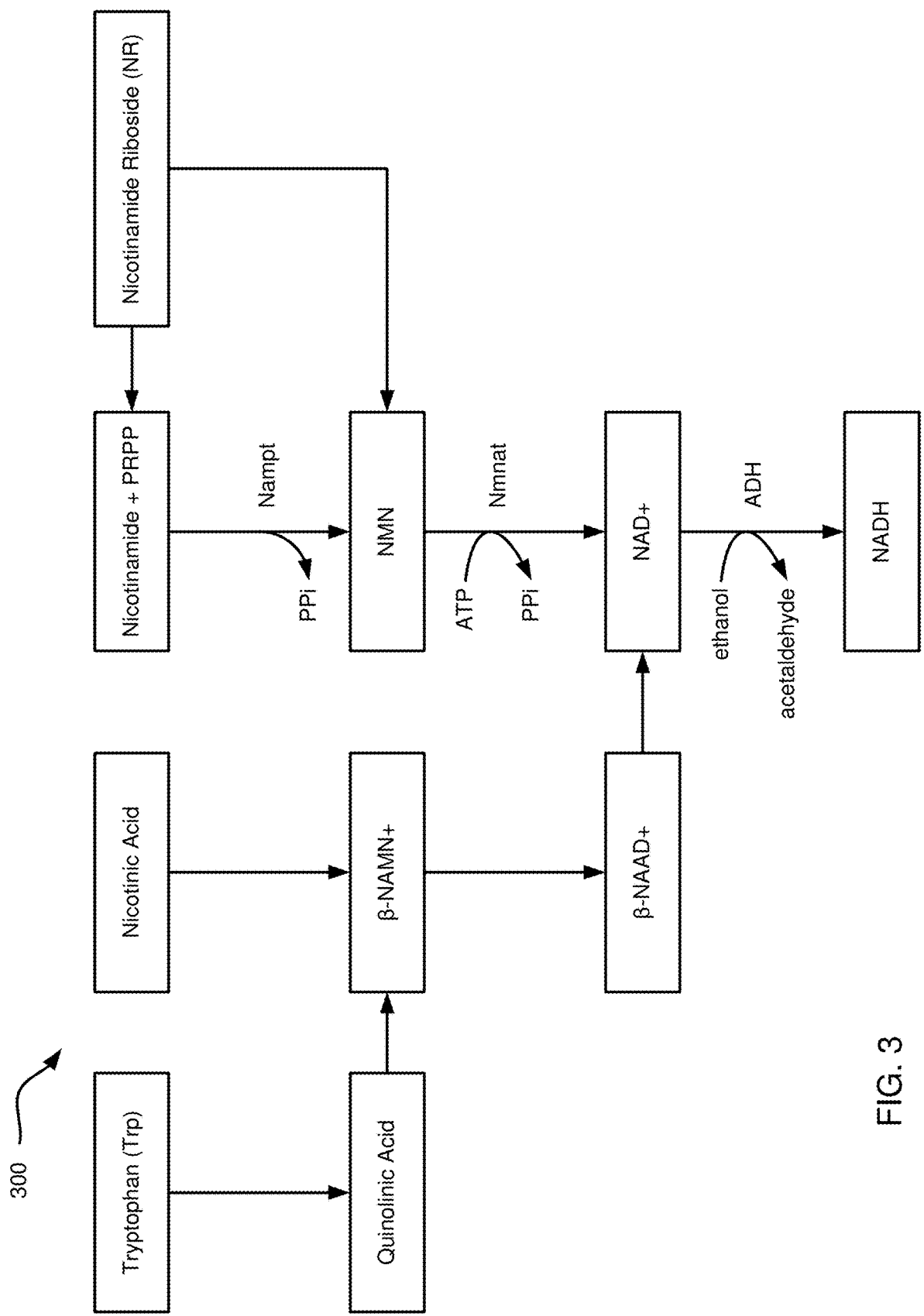
FIG. 3 is a diagram of the NAD biosynthetic and salvage pathways for regulating the production of NAD and the $NAD^+$/NADH ratio.

FIG. 3 illustrates an exemplary de novo NAD pathway 300. NAD is a cofactor that is central to metabolism. NAD is a dinucleotide including an adenine nucleobase and a nicotinamide. NAD is involved in redox reactions by carrying electrons from one reaction to another. NAD may exist as an oxidizing agent or a reducing agent. When NAD is an oxidizing agent, it accepts electrons from other molecules and becomes reduced. When NAD is a reducing agent, it donates electrons to other molecules. These electron transfer reactions are the main function of NAD.

NAD coexists in cells in two forms, including the oxidized form $NAD^+$ and the reduced form NADH. The ratio of these two forms (referred to as the $NAD^+/NADH$ ratio) is important for controlling some cellular signaling pathways. As illustrated in FIG. 3, de novo synthesis of NAD involves the amino acid tryptophan, and quinolinic acid which is generated directly from tryptophan. The quinolinic acid is converted to nicotinic acid mononucleotide (NaMN) by transfer of phosphoribosyl moiety. An adenylate moiety is transferred to form nicotinic acid adenine dinucleotide (NaAD).

An embodiment of the disclosure is a composition for activating the NAD pathway. This composition is referred to herein as the NAD composition. The NAD composition may include one or more of niacin, cuprous niacin, copper, cuprous niacin, wasabi powder, olive extract, theacrine, resveratrol, caffeine, theobromine, Yerba mate extracts, hydroxycinnamic acid, Skullcap extracts, niacin, nicotinic acid, nicotinamide, nicotinamide riboside, ribose vitamin B3, nicotinamide mononucleotide, tryptophan, quinolinic acid, beta-NAMN, and beta-NAAD, or myricetin.

In an embodiment, a composition is provided to a user for inducing a synergistic effect to increase the activation of Nrf2, NRF1, and NAD biosynthetic genes. The composition includes one or more of actyl-L-carnitine, quaternary ammonium compound, coenzyme Q10, ubiquinone, grape extract, lipoic acid, thionic acid, quercetin, calcium, silymarin, bacopa extract, ashwagandha extract root, green tea extract leaf, turmeric extract, lychee fruit extract, niacin, copper, wasabi powder, olive extract, polyphenols, flavonoids, hydroxtyrosol, theacrine, purine alkaloids, diarylheptanoid, flavonoids, proanthocyanins, resveratrol, garlic extracts, cinnamon extracts, ferulic acid, rhubarb extract, ginger extracts, ginseng extracts, Skullcap extracts, Brazilian green propolis, myricetin, cocoa extracts, caffeine, theobromine, Yerba mate extracts, hydroxycinnamic acid, Skullcap extracts, niacin, nicotinic acid, nicotinamide, nicotinamide riboside, ribose vitamin B3, nicotinamide mononucleotide, tryptophan, quinolinic acid, beta-NAMN, or beta-NAAD.

Disclosed herein are compositions and methods that provide unexpectedly good results for activating Nrf2 genes, NRF1 genes, and NAD genes. The compositions and methods disclosed herein are effective for reducing oxidative stress, improving mitochondrial activity, replacing damaged mitochondria, activating NAD biosynthetic genes, and increasing activity of sirtuins. When compared with compositions individually known to increase activity of Nrf2, NRF1, or NAD genes, the compositions and methods disclosed herein provide a synergistic effect and unexpectedly good results for increasing activity of each of Nrf2, NRF1, and NAD genes. The compositions and methods disclosed herein increase the activity of Nrf2, NRF1, and NAD genes by a greater margin than other compositions that are known to individually increase the activity of Nrf2, NRF1, or NAD genes.

Clinical Example

In one study conducted to test the effectiveness of a composition for increasing the activation of Nrf2, NRF1, and NAD genes as disclosed herein, the gene expression of each of Nrf2, NRF1, and NAD genes was greatly enhanced. In the study, human HepG2 and mouse C2C12 cells were treated in a concentration gradient (24-hour, 8-point dose-dependent curve done in quadruplicate) for cell viability to determine if the cells are sensitive to the ingredients in the composition, and to ascertain the optimal dosage for gene expression studies.

In the study, the following genes were used as markers for evaluation of treatment (see Table 1). The study included three-hour and 24-hour timepoints done in biological triplicate. The study included a control (untreated) sample, an NAD composition, an NRF1 composition, an Nrf2 composition, a combination composition with theacrine, a combination composition with alpinia galanga, a combination composition with capsaicin, and a combination composition with mango leaf extract. The study measured gene expression of the NAMPT, NMNAT, PGC1-alpha, Nrf1, NQO1, and HO1 genes.

Gene Functions Pertinent to the Study

The NAMPT (nicotinamide phosphoribosyltansferase) gene encodes a protein that catalyzes the condensation of nicotinamide with 5-phosphoribosyl-1-pyrophosphate to yield nicotinamide mononucleotide (NMN). This is one step in the biosynthesis of nicotinamide adenine dinucleotide (NAD). The protein belongs to the nicotinic acid phosphoribosyltransferase (NAPRTase) family and is thought to be involved in biological processes, including metabolism, stress response, and aging.

The NMNAT 1 (nicotinamide mononucleotide adenyltransferase-1) gene encodes an enzyme that catalyzes a step (NMN→NAD$^+$) in the biosynthesis of NAD$^+$. The encoded enzyme is one of several nicotinamide nucleotide adenyl transferases and is specifically localized to the cell nucleus. Activity of this protein leads to the activation of a nuclear deacetylase that functions in the protection of damaged cells.

The PGC1-alpha (peroxisome proliferator-activated receptor gamma coactivator 1-alpha) protein is transcriptional coactivator that regulates the genes involved in energy metabolism. The PGC1-alpha protein interacts with PAAgamma, which permits the interaction of this protein with multiple transcription factors. The PGC1-alpha protein can interact with and regulate the activities of the cAMP response element binding protein (CCB and nuclear respirator factors [NRFs]). It provides a direct link between external physiological stimuli and the regulation of mitochondrial biogenesis and is a major factor that regulates muscle fiber type determination. This protein may also be involved in controlling blood pressure, regulating cellular cholesterol homeostasis, and the development of obesity.

The Nrf1 (nuclear respirator factor-1) gene encodes a protein that homodimerizes and functions as a transcription factor that activates the expression of some metabolic genes for regulating cellular grown and nuclear genes required for respiration, heme biosynthesis, and mitochondrial DNA transcription and replication. The protein encoded by Nrf1 has also been associated with the regulation of neurite outgrowth.

The NQO1 (NAD(P)H quinone dehydrogenase-1) gene is a member of the NAD(P)H dehydrogenase (quinone) family and encodes a cytoplasmic two-electron reductase. This FAD-binding protein forms homodimers and reduces quinones to hydroquinone. This protein's enzymatic activity prevents the one electron reduction of quinones that results in the production of radical species.

The HO-1 (heme oxygenase-1) enzyme is involved in heme catabolism. The HO-1 enzyme cleaves heme to form biliverdin, which is subsequently converted to bilirubin by biliverdin reductase, and carbon monoxide, a putative neurotransmitter. Heme oxygenase activity is induced by its substrate heme and by various nonheme substances. Heme oxygenase occurs as two isozymes, an inducible heme oxygenase-1 and a constitutive heme oxygenase-2. HMOX1 and HMOX2 belong to the heme oxygenase family.

Gene Expression Assay

In the study, human HepG2 and mouse C212 cells were seeded at 200,000 cells per well. After eighteen (18) hours of incubation, the cells were treated at appropriate time points. Cells were lysed with lysis buffer and RNA (ribonucleic acid) isolations were conducted per manufacturer recommendations. The RNA isolations were conducted using the PureLink Mini RNA kit (Thermo, Cat. No. 12183025). RNA was eluted with RNase free water and qualified by spectrophotometer. Reverse transcription reactions were performed using 1 µg of RNA using the Vilo Superscript system (Thermo, Cat. No. 11756500). A six-fold dilution was made of each cDNA in PCR-grade water, and 2 µL of this solution was carried forward into qRT-PCR.

The reactions were carried out in 20 µL total volume, made up as follows: 2 µL cDNA, 6 µL PCR-grade water, 1 µL gene-of-interest primer (FAM label), 1 µL GAPDH primer (VIC label), 10 µL Taqman Fast Advanced Master Mix (Thermo Fisher Scientific, Catalog #4444963). Reactions were run on an Applied Biosystems 7500 Fast Real-Time PCR Instrument (Thermo Fisher Scientific) under the following conditions: 50° C.—2 minutes, 95° C.—20 seconds, 40 cycles of (95° C.—3 seconds, 60° C.—30 seconds). Threshold cycle (CT) was determined by the instrument software. Differences in threshold cycle between the gene of interest and GAPDH (ΔCT) were determined for each sample and used to determine fold induction of each gene of interest, compared to untreated controls.

In the study, PCR primers, were purchased from Thermo Fisher Scientific as follows: PPARGC1A (PGC-1α): Hs0106724 human Mm1208835 mouse (FAM labeled); NRF-1: Hs00602161 human Mm01135606 mouse (FAM labeled); NQO1 Hs01045993 human Mm01253561 mouse (FAM labeled); HO1: Hs011102250 human Mm00516005 mouse (FAM labeled); NAMPT: Hs00237184 human Mm00451938 mouse (FAM labeled); NMNAT1: Hs00276702 human Mm01257929 mouse (FAM labeled); NMNAT3: Hs00736183 human Mm00513791 mouse (FAM labeled); and GAPDH control: 4326315E human 4352341E mouse (VIC labeled).

In the study, the following formulas were tested for the Nrf2 composition, the NRF1 composition, the NAD composition with theacrine, the NAD composition with alpinia galanga, the NAD composition with capsaicin, and the NAD composition with mango leaf extract. The Nrf2 composition tested in the study comprised milk thistle extract, ashwagandha extract, bacopa monnieri extract, green tea extract, and turmeric extract. The NRF1 composition tested in the study comprise acetyl-L-carnitine, quercetin, grape extract, lipoic acid, and coenzyme Q10. The NAD composition with theacrine tested in the study comprised olive extract, theacrine, wasabi japonica powder, and cuprous niacin. The NAD composition with alpinia galanga tested in the study comprised alpinia galanga, wasabi powder, olive leaf extract, copper gluconate, and nicotinic acid. The NAD composition with capsaicin tested in the study comprised capsaicin, wasabi powder, olive leaf extract, nicotinic acid, and copper gluconate. The NAD composition with mango leaf extract tested in the study comprised mango leaf extract wasabi powder, olive leaf extract, nicotinic acid, and copper gluconate.

The study also included testing of combination compositions and identified overall increase in gene expression when components from the Nrf2 composition, the NRF1 composition, and one or more of the NAD compositions are combined. The combination compositions include (a) the theacrine combination; (b) the alpinia galanga combination; (c) the capsaicin combination; and (d) the mango leaf extract combination. The theacrine combination includes the components of the Nrf2 composition, the NRF1 composition, and the NAD composition with theacrine. The alpinia galanga combination includes the components of the Nrf2 composition, the NRF1 composition, and the NAD composition with alpinia galanga. The capsaicin combination includes the components of the Nrf2 composition, the NRF1 composition, and the NAD composition with capsaicin. The mango leaf extract combination includes the components of the Nrf2 composition, the NRF1 composition, and the NAD composition with mango leaf extract.

In the study, the compositions for increasing activity of the Nrf2, NRF1, and NAD genes (referred to herein as the combination compositions) exhibited unexpectedly good results for increasing activity of each of the Nrf2, NRF1, and NAD genes. The combination compositions increased the activity of each of the Nrf2 genes, the NRF1 genes, and the NAD genes at a greater rate than any of the Nrf2 composition, the NRF1 composition, or the NAD compositions alone. Said another way, the combination composition increased the activity of the Nrf2 target genes at a greater rate than the Nrf2 composition alone. Further, the combination compositions increased the activity of the NRF1 genes at a greater rate than the NRF1 composition alone. Further, the combination compositions increased the activity of the NAD genes at a greater rate than the NAD composition alone. Therefore, the combination compositions exhibited an unexpected synergistic effect for increasing activity of each of the Nrf2, NRF1, and NAD genes.

Figures 7A, 7B:
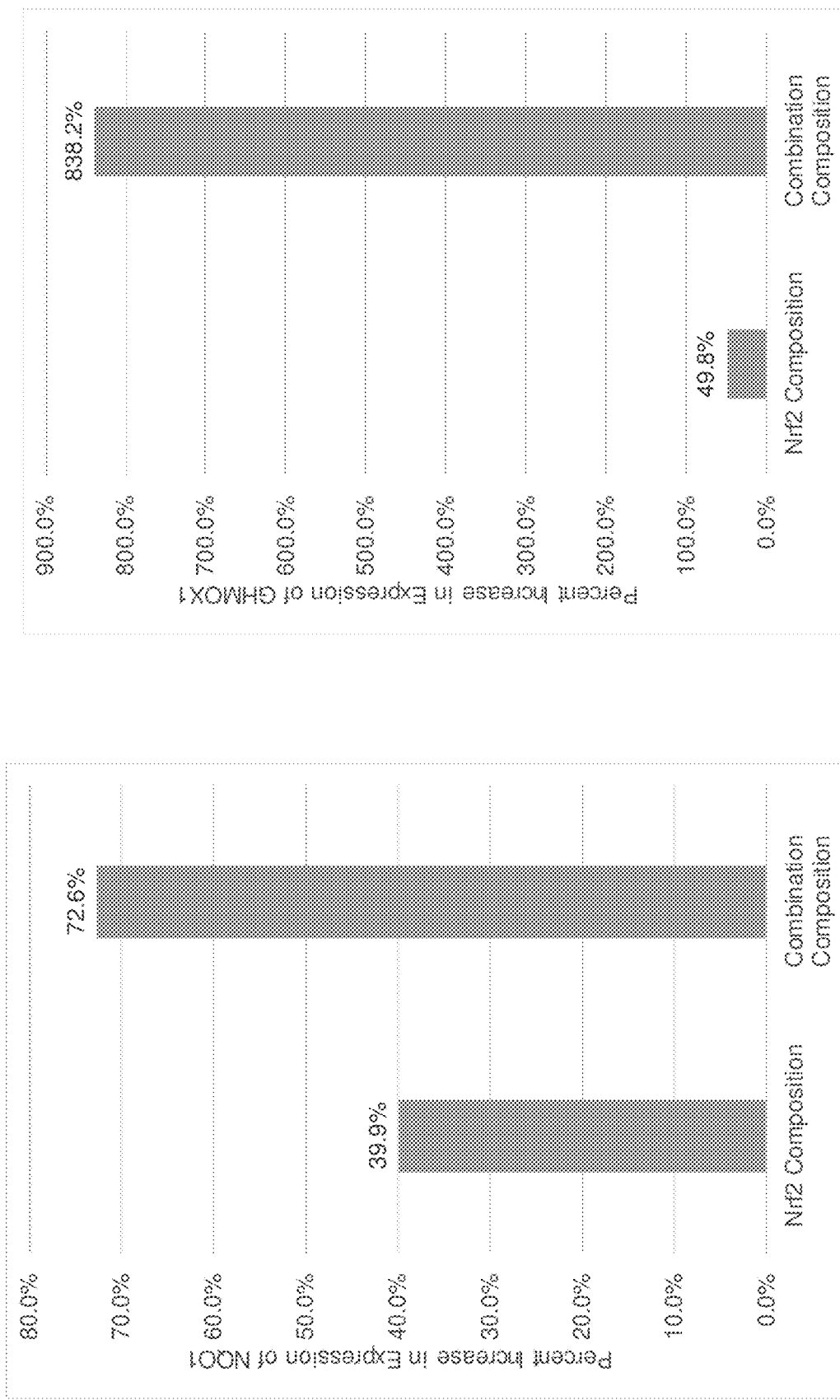
FIG. 7A is a bar graph illustrating the percent increase in expression of the NQO1 gene 24 hours after administration of the Nrf2 composition and the combination composition as disclosed herein.
FIG. 7B is a bar graph illustrating the percent increase in expression of the HMOX1 gene 24 hours after administration of the Nrf2 composition and the combination composition as disclosed herein.
Figures 8A, 8B:
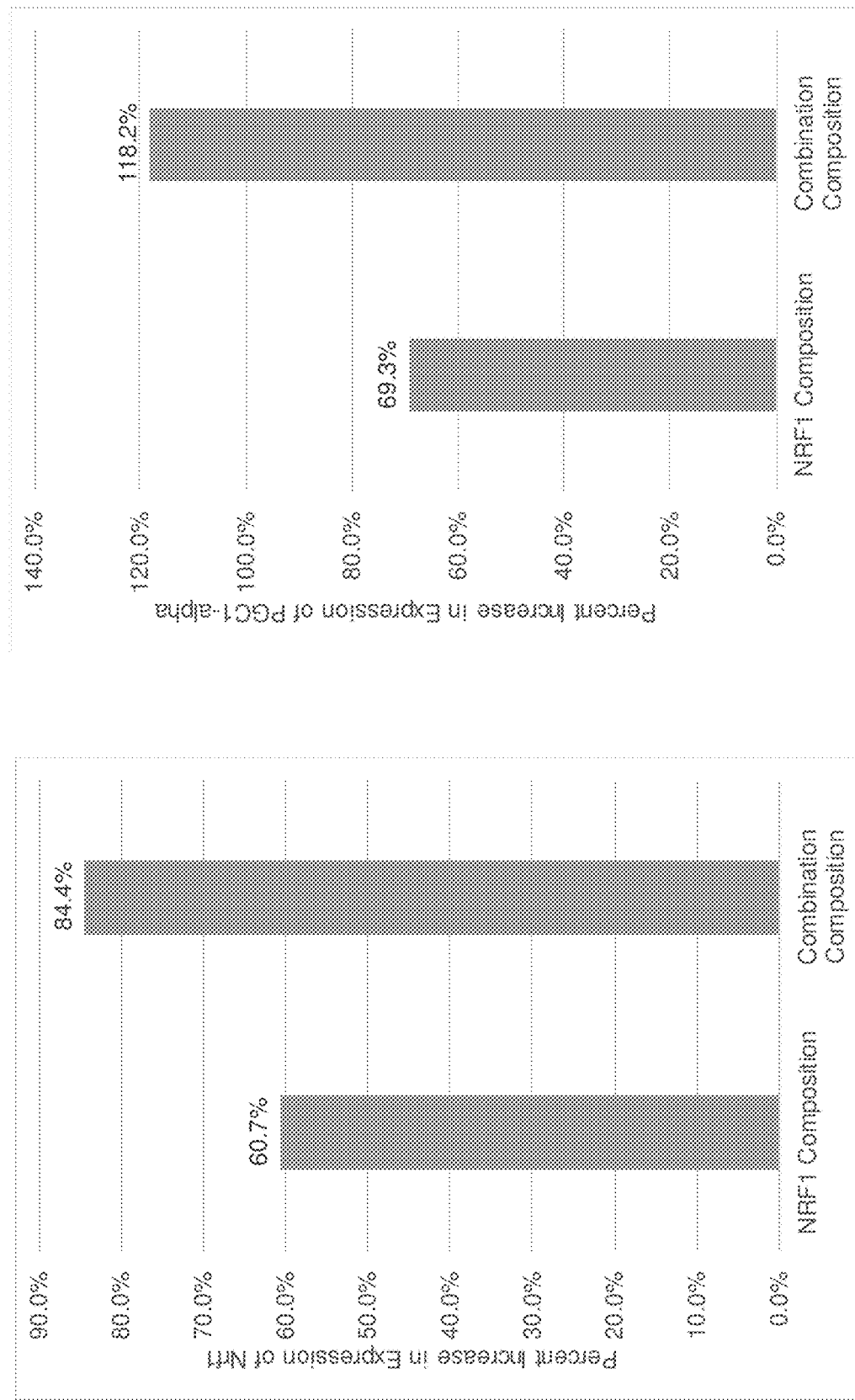
FIG. 8A is a bar graph illustrating the percent increase in expression of the Nrf1 gene 24 hours after administration of the NRF1 composition and the combination composition as disclosed herein.
FIG. 8B is a bar graph illustrating the percent increase in expression of the hPGC1-alpha gene 24 hours after administration of the NRF1 composition and the combination composition as disclosed herein.
Figure 9A:
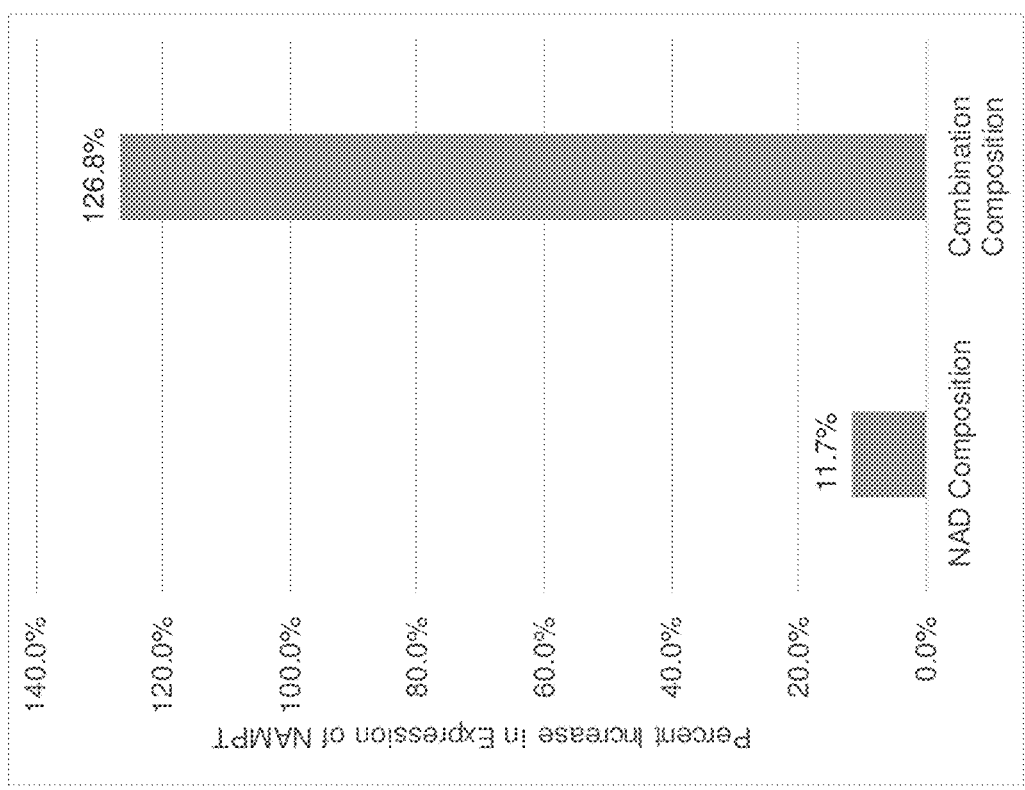
FIG. 9A is a bar graph illustrating the percent increase in expression of the NMNAT1 gene 24 hours after administration of the NAD composition and the combination composition as disclosed herein.
Figure 9B:
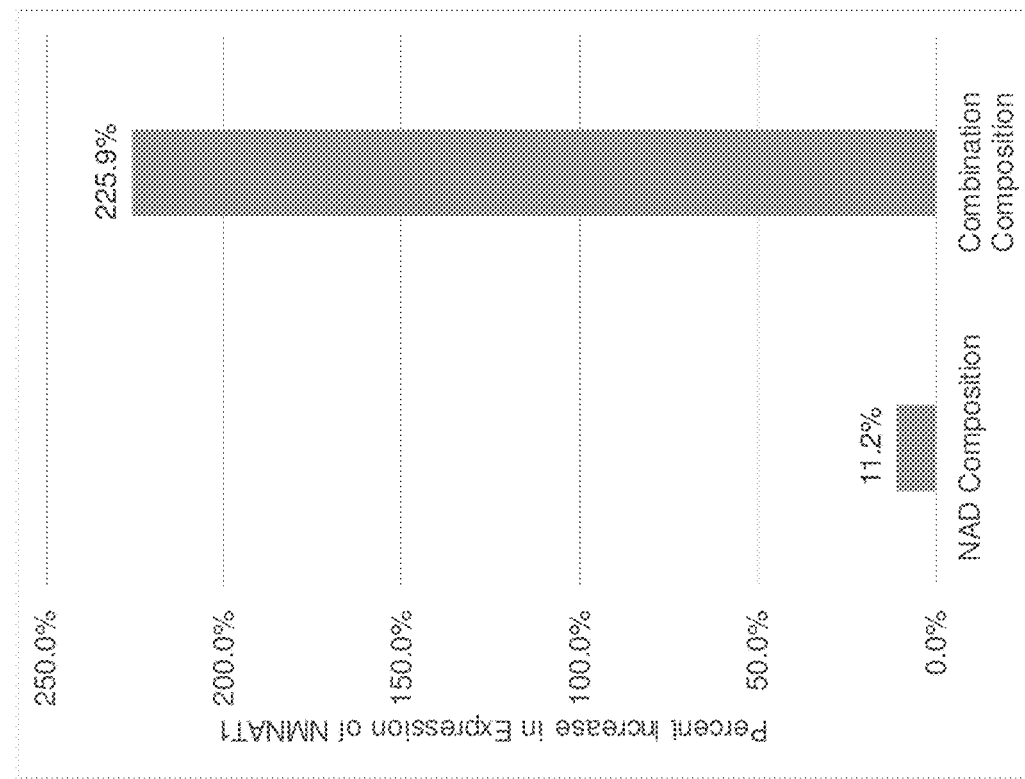
FIG. 9B is a bar graph illustrating the percent increase in expression of the NAMPT gene 24 hours after administration of the NAD composition and the combination composition as disclosed herein.

FIGS. 4A-9B illustrate results of the clinical study. The test results for the combination composition illustrated in FIGS. 4A-9B apply to the theacrine combination including the Nrf2 composition, the NRF1 composition, and the NAD composition comprising theacrine. FIGS. 4A-4B are bar graphs indicating the percent increase in activation of the Nrf2 pathway in response to the Nrf2 composition and the combination composition after three hours. FIGS. 5A-5B are bar graphs indicating the percent increase in the activation of the NRF1 pathway in response to the NRF1 composition and the combination composition after three hours. FIGS. 6A-6B are bar graphs indicating the percent increase in activation of the NAD pathway in response to the NAD composition and the combination composition after three hours. FIGS. 7A-7B are bar graphs indicating the percent increase in activation of the Nrf2 pathway in response to the Nrf2 composition and the combination composition after 24 hours. FIGS. 8A-8B are bar graphs indicating the percent increase in the activation of the NRF1 pathway in response to the NRF1 composition and the combination composition after 24 hours. FIGS. 9A-9B are bar graphs indicating the percent increase in activation of the NAD pathway in response to the NAD composition and the combination composition after 24 hours.

FIGS. 4A-4B are bar graphs illustrating the comparative percent increases to activation of the Nrf2 pathway in response to the Nrf2 composition and the combination composition. The data illustrated in FIGS. 4A-4B is based on HepG2 cells at 10 μg/mL for three hours. FIG. 4A illustrates the percent increase in expression of the NQO1 gene in response to the Nrf2 composition and the combination composition. As shown, the Nrf2 composition causes a 30.6% increase in expression of the NQO1 gene over three hours. The combination composition causes a 32.5% increase in expression of the NQO1 gene over three hours. There is a 6.2% increase in expression of the NQO1 gene by the combination composition when compared with the Nrf2 composition. FIG. 4B illustrates the percent increase in expression of the HMOX1 gene in response to the Nrf2 composition and the combination composition. As shown, the Nrf2 composition causes a 502.2% increase in expression of the HMOX1 gene over three hours. The combination composition causes an 867.2% increase in expression of the HMOX1 gene over three hours. There is a 72.7% increase in expression of the NQO1 gene by the combination composition when compared with the Nrf2 composition.

Figures 5A, 5B:
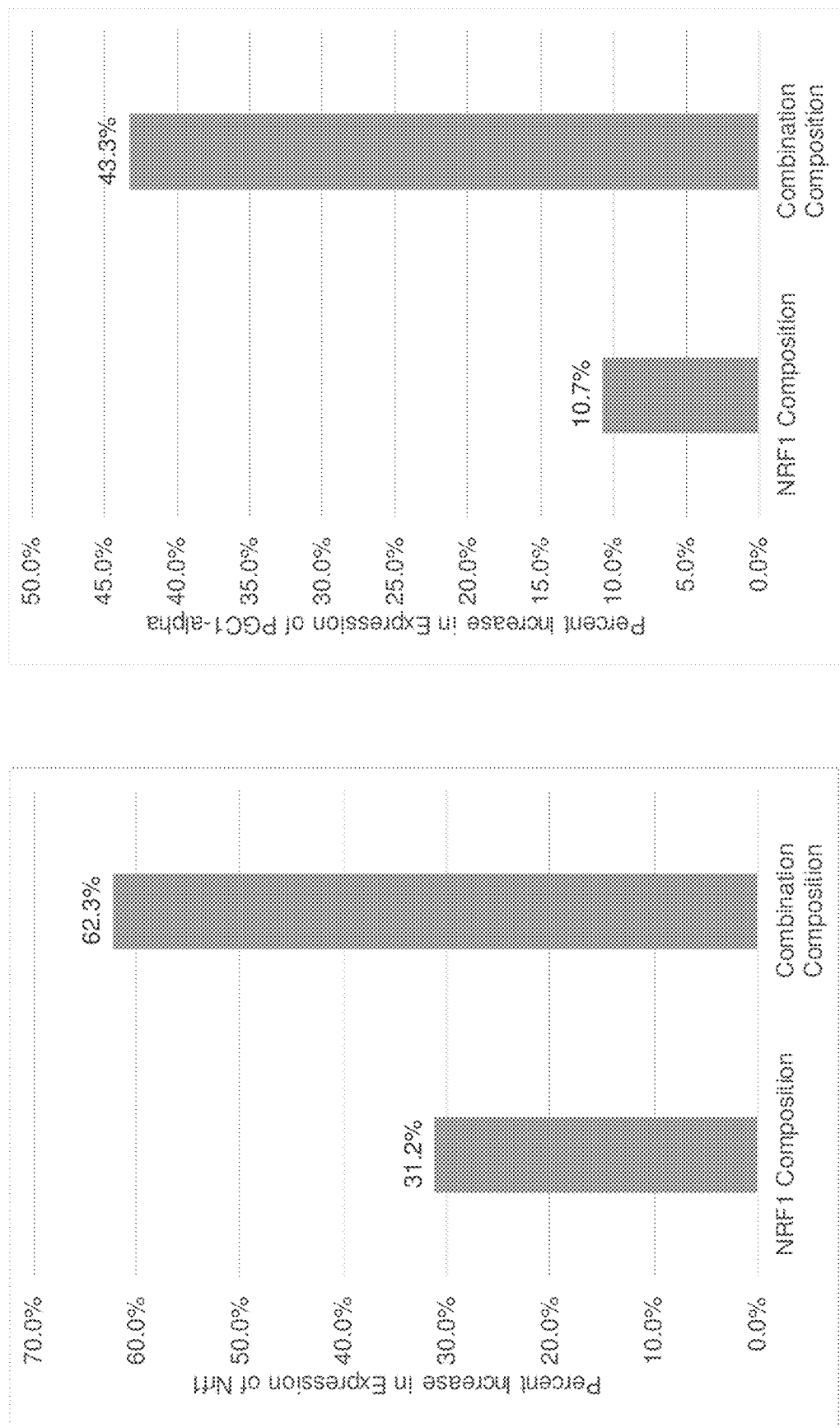
FIG. 5A is a bar graph illustrating the percent increase in expression of the Nrf1 gene three hours after administration of the NRF1 composition and the combination composition as disclosed herein.
FIG. 5B is a bar graph illustrating the percent increase in expression of the hPGC1-alpha gene three hours after administration of the NRF1 composition and the combination composition as disclosed herein.

FIGS. 5A-5B are bar graphs illustrating the comparative percent increases to activation of the NRF1 pathway in response to the NRF1 composition and the combination composition. The data illustrated in FIGS. 5A-5B is based on HepG2 cells at 10 μg/mL for three hours. FIG. 5A illustrates the percent increase in expression of the Nrf1 gene in response to the NRF1 composition and the combination composition. As shown, the NRF1 composition causes a 31.2% increase in expression of the Nrf1 gene over three hours. The combination composition causes a 62.3% increase in expression of the Nrf1 gene over three hours. There is a 99.8% increase in expression of the Nrf1 gene by the combination composition when compared with the NRF1 composition. FIG. 5B illustrates the percent increase in expression of the PGC1-alpha gene in response to the NRF1 composition and the combination composition. As shown, the NRF1 composition causes a 10.7% increase in expression of the PGC1-alpha gene over three hours. The combination composition causes a 43.3% increase in expression of the PGC1-alpha gene over three hours. There is a 304.8% increase in expression of the PGC1-alpha gene by the combination composition when compared with the NRF1 composition.

FIGS. 6A-6B are bar graphs illustrating the comparative percent increases to activation of the NAD pathway in response to the NAD composition and the combination composition. The data illustrated in FIGS. 6A-6B is based on HepG2 cells at 10 µg/mL for three hours. FIG. 6A illustrates the percent increase in expression of the NMNAT1 gene in response to the NAD composition and the combination composition. As shown, the NAD composition causes a 7.5% increase in expression of the NMNAT1 gene over three hours. The combination composition causes a 90.9% increase in expression of the NMNAT1 gene over three hours. There is a 1104.1% increase in expression of the NMNAT1 gene by the combination composition when compared with the NAD composition. FIG. 6B illustrates the percent increase in expression of the NAMPT gene in response to the NAD composition and the combination composition. As shown, the NAD composition causes a 1.9% increase in expression of the NAMPT gene over three hours. The combination composition causes a 21.1% increase in expression of the NAMPT gene over three hours. There is a 1011.0% increase in expression of the NAMPT gene by the combination composition when compared with the NAD composition.

FIGS. 7A-7B are bar graphs illustrating the comparative percent increases to activation of the Nrf2 pathway in response to the Nrf2 composition and the combination composition. The data illustrated in FIGS. 4A-4B is based on HepG2 cells at 10 µg/mL for 24 hours. FIG. 7A illustrates the percent increase in expression of the NQO1 gene in response to the Nrf2 composition and the combination composition. As shown, the Nrf2 composition causes a 39.9% increase in expression of the NQO1 gene over 24 hours. The combination composition causes a 72.6% increase in expression of the NQO1 gene over 24 hours. There is an 82.1% increase in expression of the NQO1 gene by the combination composition when compared with the Nrf2 composition. FIG. 7B illustrates the percent increase in expression of the HMOX1 gene in response to the Nrf2 composition and the combination composition. As shown, the Nrf2 composition causes a 49.8% increase in expression of the HMOX1 gene over 24 hours. The combination composition causes an 838.2% increase in expression of the HMOX1 gene over 24 hours. There is a 1582.5% increase in expression of the NQO1 gene by the combination composition when compared with the Nrf2 composition.

FIGS. 8A-8B are bar graphs illustrating the comparative percent increases to activation of the NRF1 pathway in response to the NRF1 composition and the combination composition. The data illustrated in FIGS. 8A-8B is based on HepG2 cells at 10 µg/mL for 24 hours. FIG. 8A illustrates the percent increase in expression of the Nrf1 gene in response to the NRF1 composition and the combination composition. As shown, the NRF1 composition causes a 60.7% increase in expression of the Nrf1 gene over 24 hours. The combination composition causes an 84.4% increase in expression of the Nrf1 gene over 24 hours. There is a 39.2% increase in expression of the Nrf1 gene by the combination composition when compared with the NRF1 composition. FIG. 8B illustrates the percent increase in expression of the PGC1-alpha gene in response to the NRF1 composition and the combination composition. As shown, the NRF1 composition causes a 69.3% increase in expression of the PGC1-alpha gene over 24 hours. The combination composition causes a 118.2% increase in expression of the PGC1-alpha gene over 24 hours. There is a 70.7% increase in expression of the PGC1-alpha gene by the combination composition when compared with the NRF1 composition.

FIGS. 9A-9B are bar graphs illustrating the comparative percent increases to activation of the NAD pathway in response to the NAD composition and the combination composition. The data illustrated in FIGS. 9A-9B is based on HepG2 cells at 10 µg/mL for 24 hours. FIG. 9A illustrates the percent increase in expression of the NMNAT1 gene in response to the NAD composition and the combination composition over 24 hours. As shown, the NAD composition causes an 11.2% increase in expression of the NMNAT1 gene over 24 hours. The combination composition causes a 225.9% increase in expression of the NMNAT1 gene over 24 hours. There is a 1915.6% increase in expression of the NMNAT1 gene by the combination composition when compared with the NAD composition. FIG. 9B illustrates the percent increase in expression of the NAMPT gene in response to the NAD composition and the combination composition. As shown, the NAD composition causes a 11.7% increase in expression of the NAMPT gene over 24 hours. The combination composition causes a 126.8% increase in expression of the NAMPT gene over 24 hours. There is a 986.8% increase in expression of the NAMPT gene by the combination composition when compared with the NAD composition.

FIGS. 10-15 further illustrate results of the study. The test results illustrated in FIGS. 10-15 include results for each of the four potential combination compositions, including the theacrine combination, the alpinia combination, the capsaicin combination, and the mango combination. The theacrine combination includes the NRF1 composition, the Nrf2 composition, and the theacrine NAD composition. The alpinia combination includes the NRF1 composition, the Nrf2 composition, and the alpinia galanga NAD composition. The capsaicin combination includes the NRF1 composition, the Nrf2 composition, and the capsaicin NAD composition. The mango combination includes the NRF1 composition, the Nrf2 composition, and the mango leaf extract NAD composition.

Figure 10:
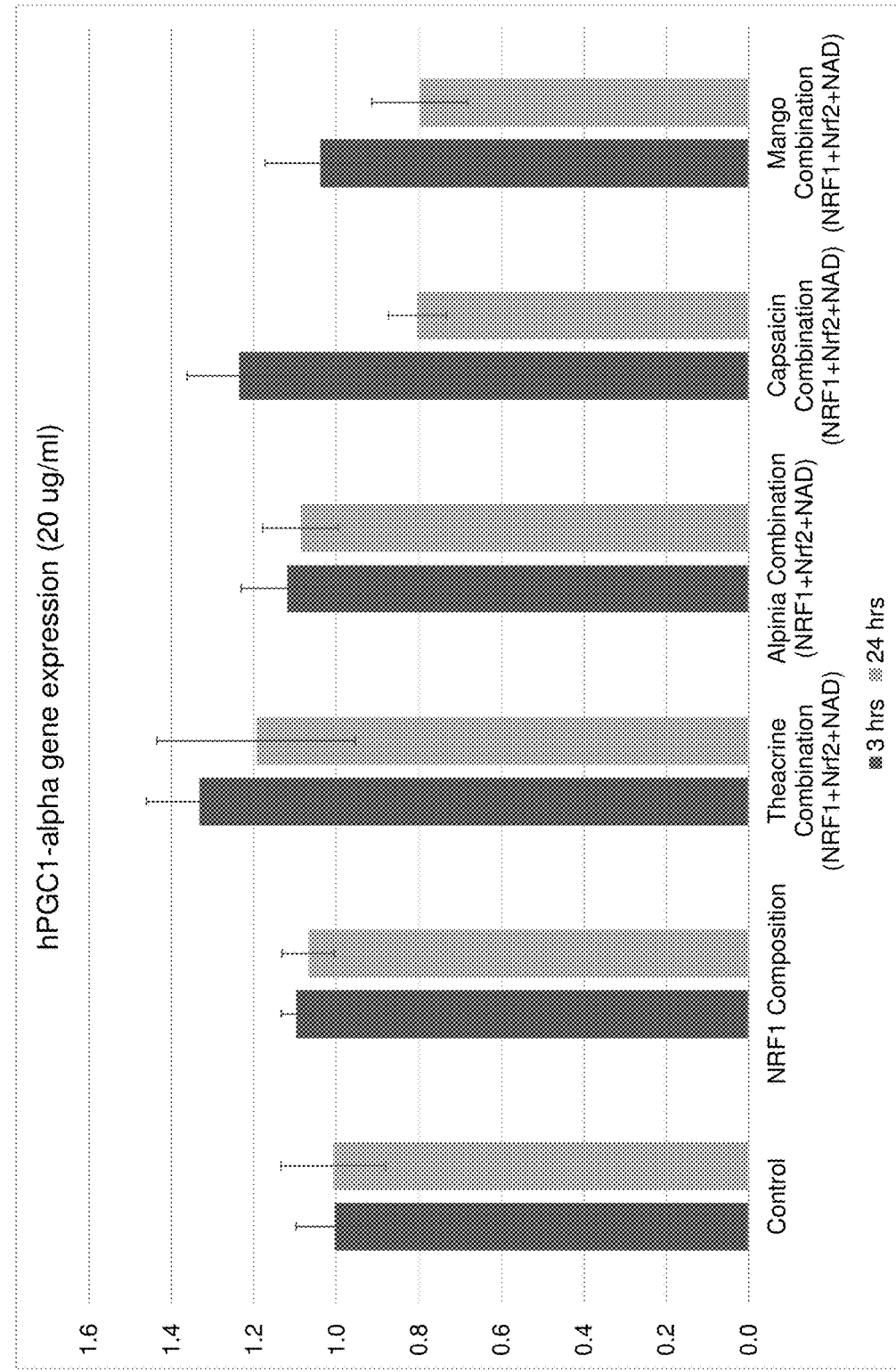
FIG. 10 is a bar graph illustrating expression of the hPGC1-alpha gene three hours and 24 hours after administration of a control, an NRF1 composition, a theacrine combination composition, an alpinia galanga combination composition, a capsaicin combination composition, and a mango leaf extract combination composition as disclosed herein.

FIG. 10 illustrates results for activation of hPGC1-alpha gene expression by treating HepG2 cells with 20 µg/mL for three hours and 24 hours. As illustrated in FIG. 10, the NRF1 composition provided some marginal increase in hPGC1-alpha gene expression when compared with the control. However, each of the combination compositions, including the theacrine combination, the alpinia combination, the capsaicin combination, and the mango combination, provided unexpectedly good results and further increase in hPGC1-alpha gene expression when compared with the NRF1 composition alone.

Figure 11:
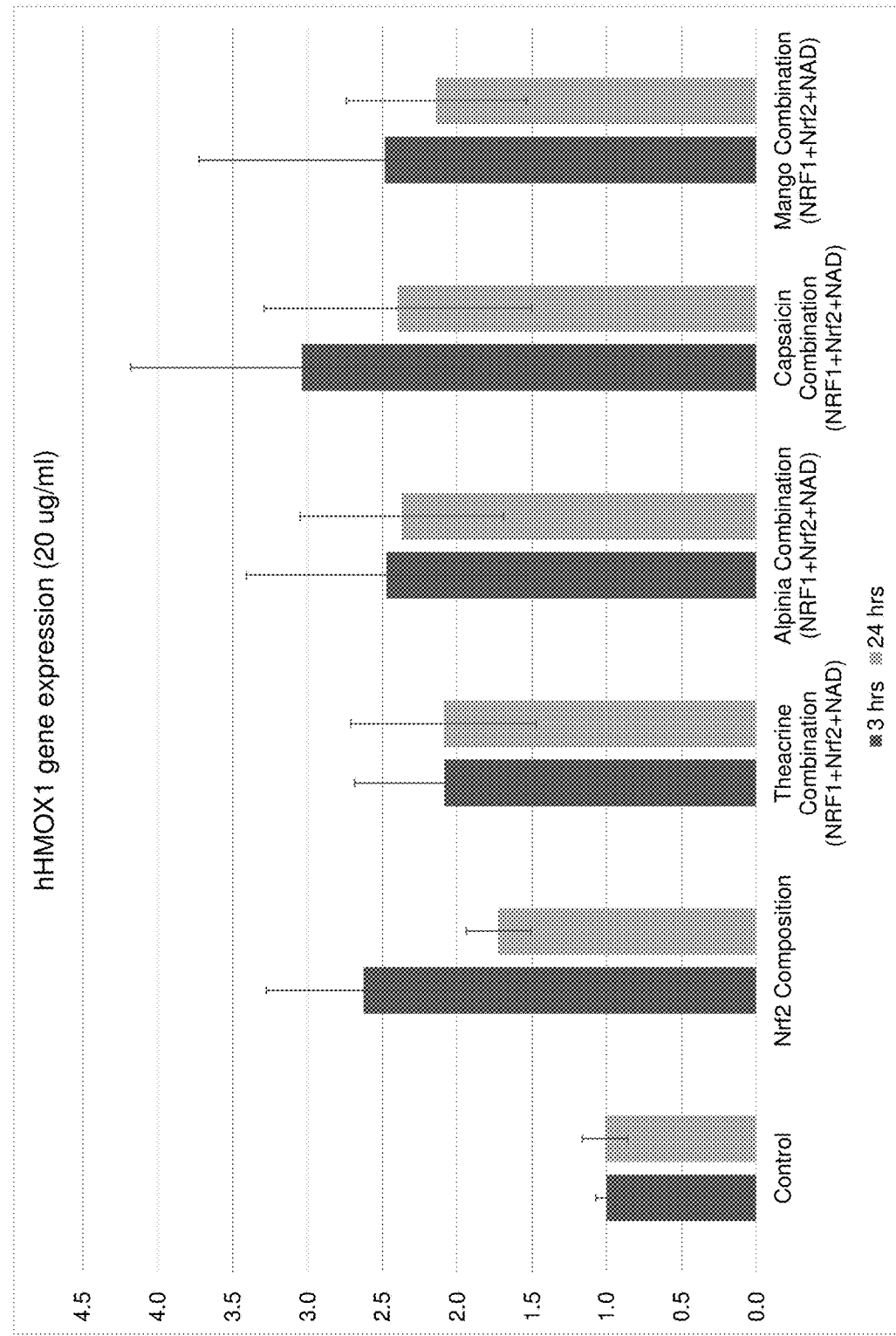
FIG. 11 is a bar graph illustrating expression of the hHMOX1 gene three hours and 24 hours after administration of a control, an Nrf2 composition, a theacrine combination composition, an alpinia galanga combination composition, a capsaicin combination composition, and a mango leaf extract combination composition as disclosed herein.

FIG. 11 illustrates results for activation of hHMOX1 gene expression by treating HepG2 cells with 20 µg/mL for three hours and 24 hours. As illustrated in FIG. 11, the Nrf2 composition enabled increased expression of the hHMOX1 gene when compared with the control. However, each of the combination compositions, including the theacrine combination, the alpinia combination, the capsaicin combination, and the mango combination, provided unexpectedly good results and further increase in hHMOX1 gene expression when compared with the Nrf2 composition alone.

Figure 12:
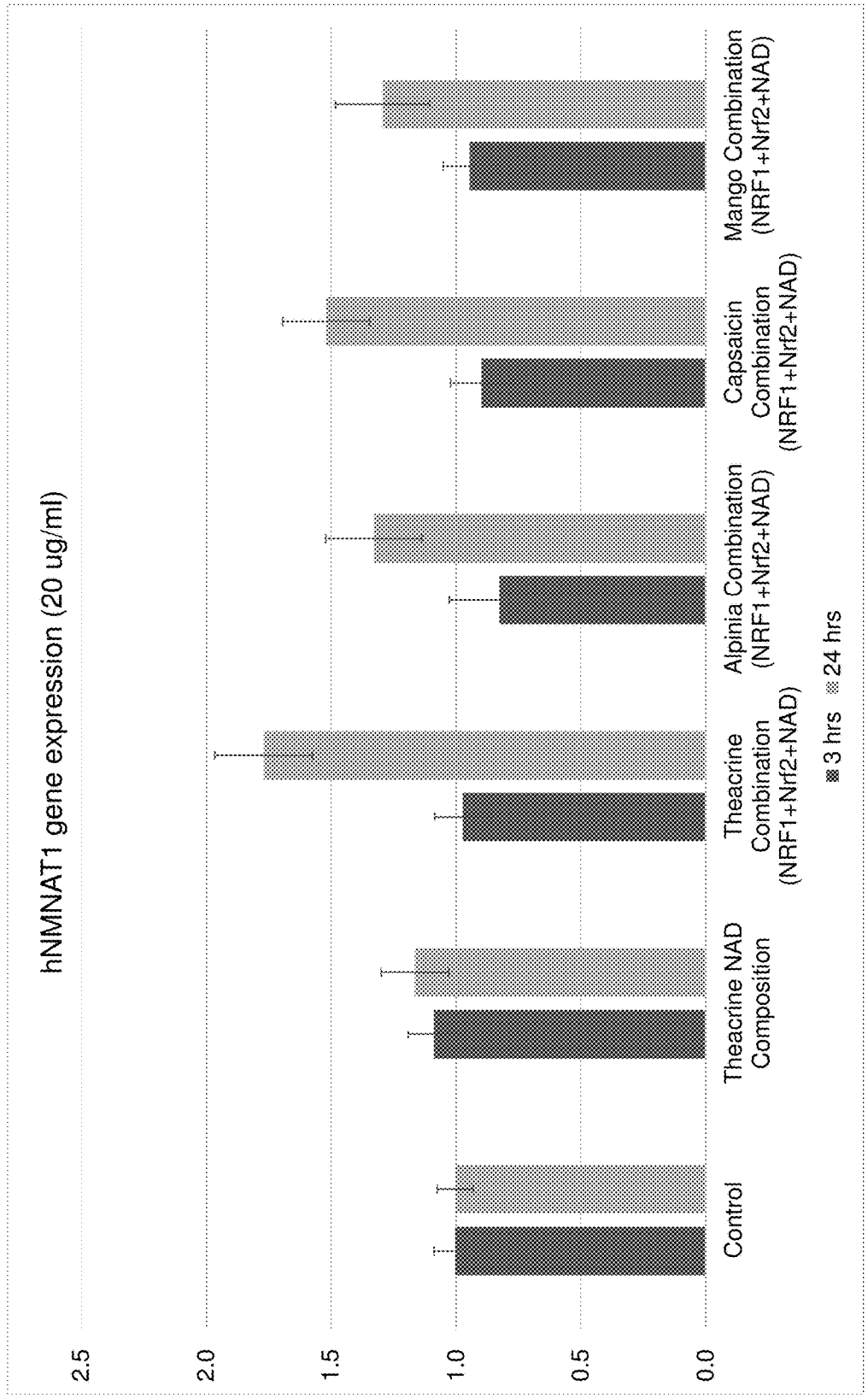
FIG. 12 is a bar graph illustrating expression of the hNMNAT1 gene three hours and 24 hours after administration of a control, a theacrine NAD composition, a theacrine combination composition, an alpinia galanga combination composition, a capsaicin combination composition, and a mango leaf extract combination composition as disclosed herein.

FIG. 12 illustrates results for activation of hNMNAT1 gene expression by treating HepG2 cells with 20 µg/mL for three hours and 24 hours. As illustrated in FIG. 12, the NAD composition comprising theacrine enabled increased expression of the hNMNAT1 gene when compared with the control. However, each of the combination compositions, including the theacrine combination, the alpinia combination, the capsaicin combination, and the mango combination, provided unexpectedly good results and further increase in hNMNAT1 gene expression when compared with the NAD composition comprising theacrine alone.

Figure 13:
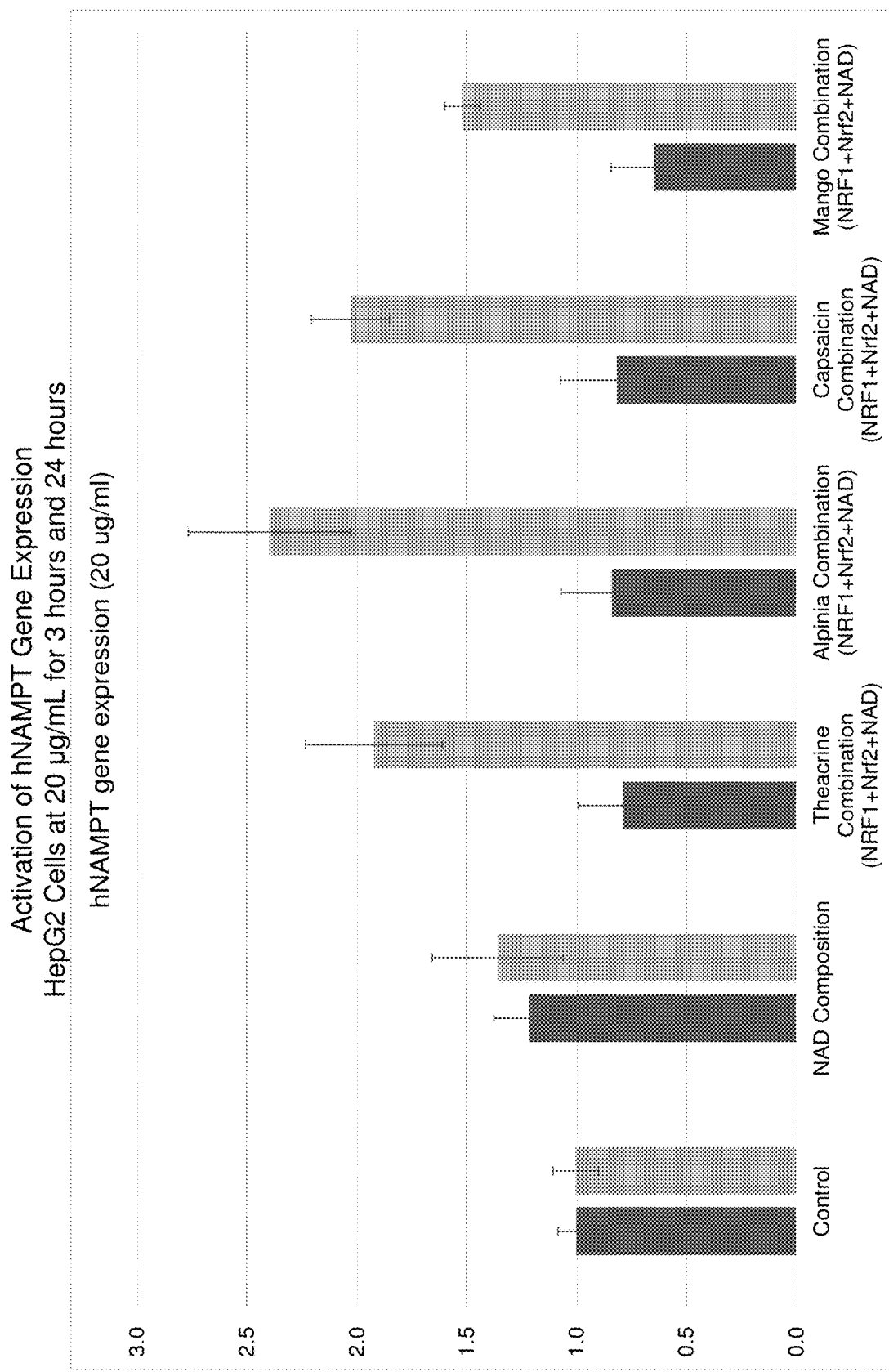
FIG. 13 is a bar graph illustrating expression of the hNAMPT gene three hours and 24 hours after administration of a control, a theacrine NAD composition, a theacrine combination composition, an alpinia galanga combination composition, a capsaicin combination composition, and a mango leaf extract combination composition as disclosed herein.

FIG. 13 illustrates results for activation of hNAMPT gene expression by treating HepG2 cells with 20 μg/mL for three hours and 24 hours. As illustrated in FIG. 13, the NAD composition comprising theacrine enabled increased expression of the hNAMPT gene when compared with the control. However, each of the combination compositions, including the theacrine combination, the alpinia combination, the capsaicin combination, and the mango combination, provided unexpectedly good results and further increase in hNAMPT gene expression when compared with the NAD composition comprising theacrine alone.

Figure 14:
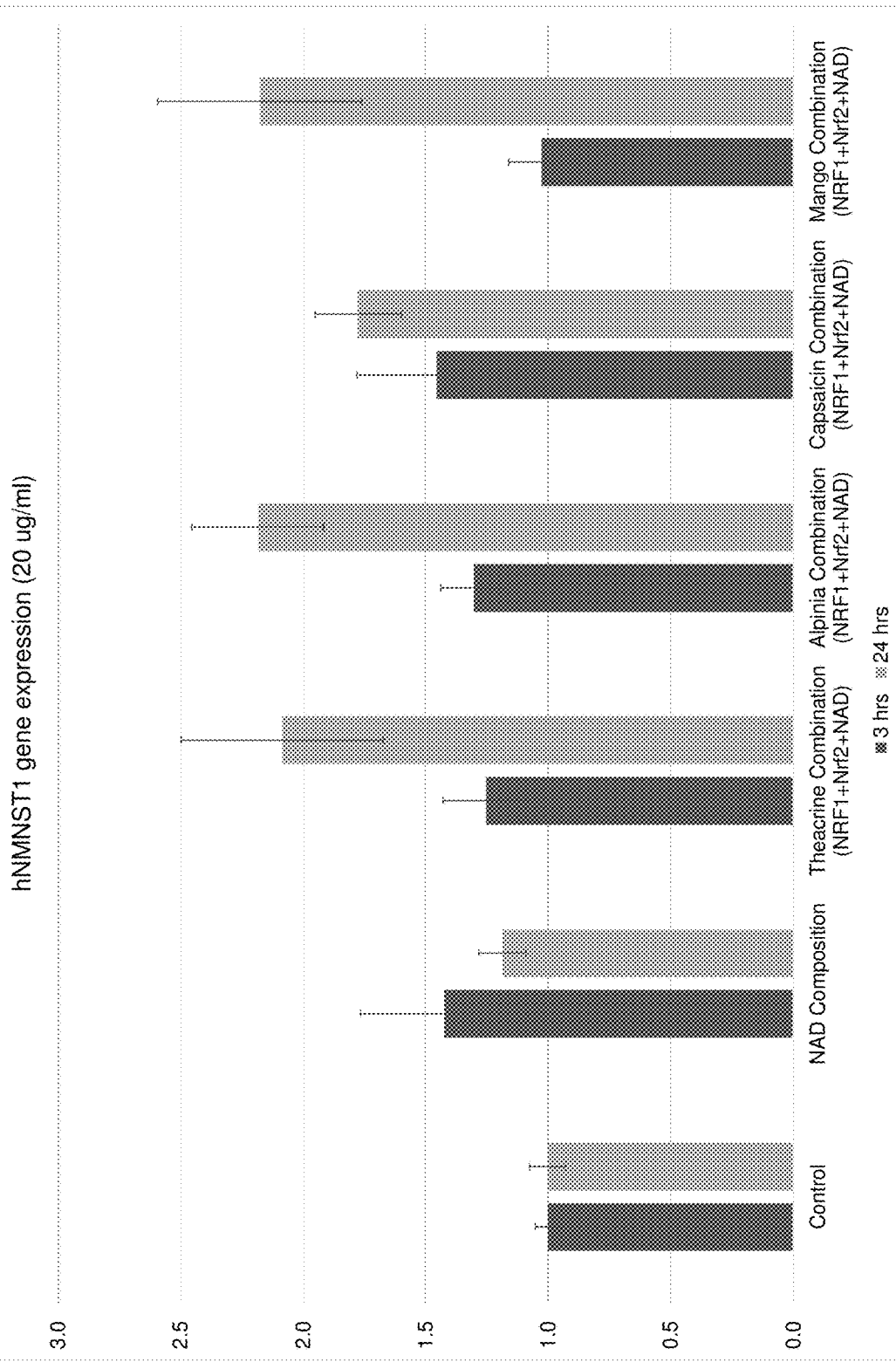
FIG. 14 is a bar graph illustrating expression of the hNMNST1 gene three hours and 24 hours after administration of a control, a theacrine NAD composition, a theacrine combination composition, an alpinia galanga combination composition, a capsaicin combination composition, and a mango leaf extract combination composition as disclosed herein.
Figure 15:
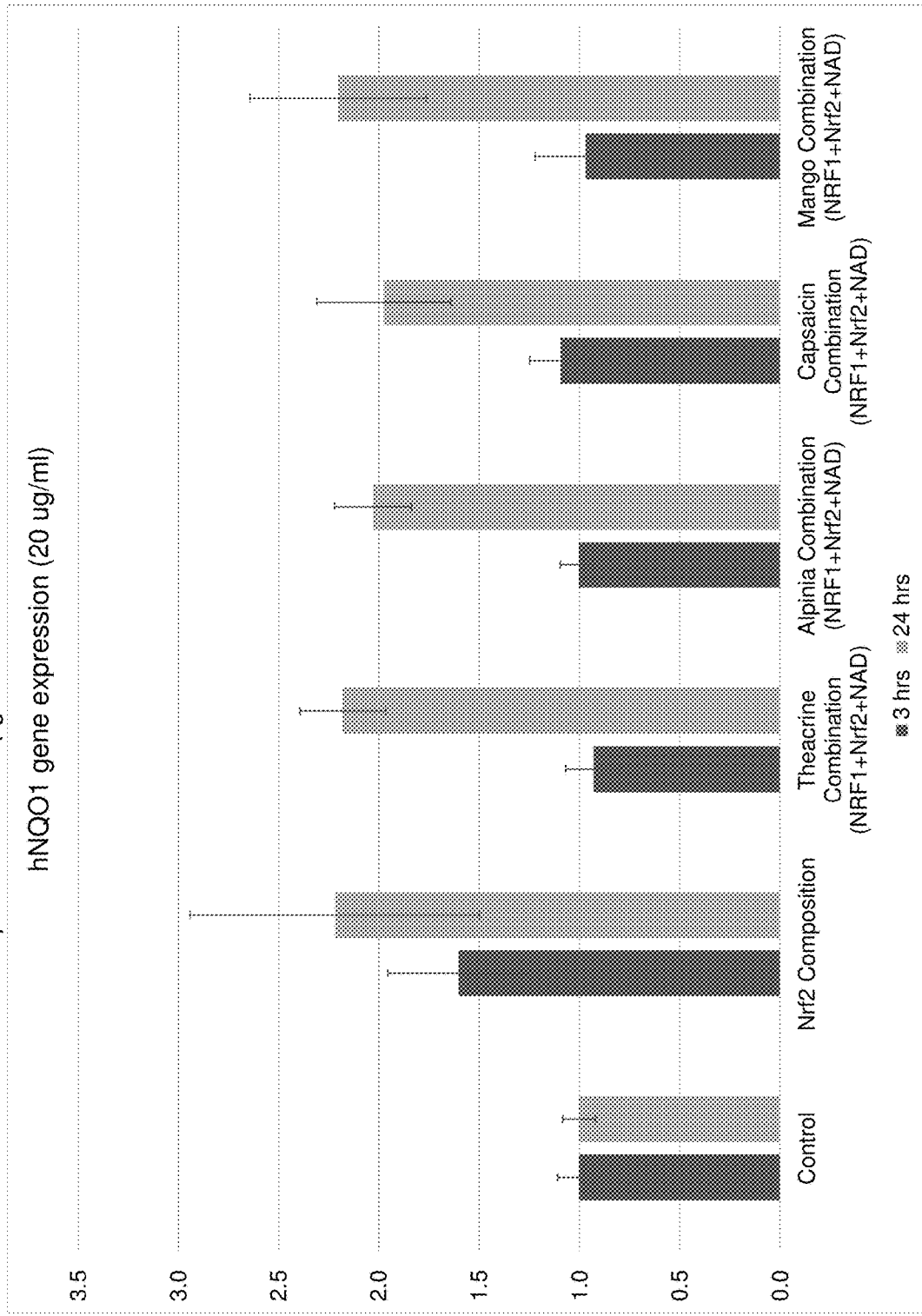
FIG. 15 is a bar graph illustrating expression of the hNQO1 gene three hours and 24 hours after administration of a control, an Nrf2 composition, a theacrine combination composition, an alpinia galanga combination composition, a capsaicin combination composition, and a mango leaf extract combination composition as disclosed herein.

FIG. 14 illustrates results for activation of hNMNST1 gene expression by treating HepG2 cells with 20 μg/mL for three hours and 24 hours. As illustrated in FIG. 15, the NAD composition comprising theacrine enabled increased expression of the hNMNST1 gene when compared with the control. However, each of the combination compositions, including the theacrine combination, the alpinia combination, the capsaicin combination, and the mango combination, provided unexpectedly good results and further increase in hNMNST1 gene expression when compared with the NAD composition comprising theacrine alone.

FIG. 15 illustrates results for activation of hNQO1 gene expression by treating HepG2 cells with 20 μg/mL for three hours and 24 hours. As illustrated in FIG. 16, the Nrf2 composition enabled increased expression of the hNQO1 gene when compared with the control. However, each of the combination compositions, including the theacrine combination, the alpinia combination, the capsaicin combination, and the mango combination, provided unexpectedly good results and further increase in hNQO1 gene expression when compared with the Nrf2 composition alone.

EXAMPLES

The following examples pertain to further embodiments. As discussed in the example embodiments, the "composition" may refer to one or more of the compositions described herein, including the theacrine combination, the alpinia galanga combination, the capsaicin combination, and the mango leaf extract combination.

Table 1 below shows an example embodiment of the composition.

TABLE 1

| Component | Weight Percent in Blend |
| --- | --- |
| Ashwagandha extract | 7.6 |
| *Bacopa monnieri* extract | 7.8 |
| Green tea extract | 3.9 |
| Turmeric extract | 3.9 |
| Acetyl-L-Carnitine | 26.0 |
| Quercetin | 7.3 |
| Grape extract | 3.6 |
| Lipoic acid | 2.6 |
| Coenzyme Q10 | 1.6 |
| Olive leaf extract | 7.8 |
| Theacrine | 6.5 |

TABLE 1-continued

| Component | Weight Percent in Blend |
| --- | --- |
| Wasabi japonica powder | 9.6 |
| Cuprous niacin | 0.1 |
| Milk Thistle Extract | 11.7 |

Table 2 below shows an example embodiment of the composition.

TABLE 2

| Component | Weight Percent Total Composition |
| --- | --- |
| Milk thistle extract | 11.5 |
| Ashwagandha extract | 7.7 |
| *Bacopa monnieri* extract | 7.7 |
| Green tea extract | 3.8 |
| Turmeric extract | 3.8 |
| Hydroxypropyl methylcellulose | 0.5 |
| Calcium | 7.9 |
| Calcium carbonate gran | 6.1 |
| Microcrystalline cellulose | 5.1 |
| Croscarmellose sodium | 1.5 |
| Silica | 0.5 |
| Medium chain triglycerides | 0.5 |
| Magnesium | 0.7 |
| Purified water | 3.8 |
| Acetyl-L-carnitine | 12.8 |
| Quercetin | 3.6 |
| Lipoic acid | 1.3 |
| Coenzyme Q10 | 0.8 |
| Grape extract | 1.8 |
| Wasabi rhizome powder | 5.1 |
| Theacrine | 3.1 |
| Copper niacin complex | 0.1 |
| Olive extract | 3.8 |
| Rice flour | 6.3 |
| Syloid | 0.2 |

Table 3 below shows an example embodiment of the composition.

TABLE 3

| Component | Weight Percent in Blend |
| --- | --- |
| Acetyl-L-Carnitine | 32.9 |
| Quercetin | 3.2 |
| Grape | 2.3 |
| Lipoic acid | 0.3 |
| Coenzyme Q10 | 0.1 |
| Milk Thistle | 8.5 |
| Ashwagandha | 4.2 |
| *Bacopa monnieri* | 4.8 |
| Green Tea | 13.5 |
| Turmeric | 8.6 |
| Wasabi japonica | 8.4 |
| Olive leaf | 7.5 |
| Theacrine | 5.7 |
| Copper Niacin Complex | 0.0002 |

Table 4 below shows an example embodiment of the composition.

TABLE 4

| Component | Weight Percent in Blend |
| --- | --- |
| Acetyl-L-Carnitine | 2.2 |
| Quercetin | 0.2 |
| Grape | 0.04 |

TABLE 4-continued

| Component | Weight Percent in Blend |
|---|---|
| Lipoic acid | 0.02 |
| Coenzyme Q10 | 0.008 |
| Milk Thistle | 0.5 |
| Ashwagandha | 0.2 |
| Bacopa monnieri | 0.2 |
| Green Tea | 0.05 |
| Turmeric | 0.05 |
| Wasabi japonica | 0.3 |
| Olive leaf | 0.2 |
| Theacrine | 0.1 |
| Copper Niacin Complex | 0.000008 |

Table 5 below shows an example embodiment of the composition.

TABLE 5

| Component | Weight Percent in Blend |
|---|---|
| Acetyl-L-Carnitine | 12.3 |
| Quercetin | 1.0 |
| Grape | 0.2 |
| Lipoic acid | 0.1 |
| Coenzyme Q10 | 0.04 |
| Milk Thistle | 2.9 |
| Ashwagandha | 1.3 |
| Bacopa monnieri | 1.2 |
| Green Tea | 0.3 |
| Turmeric | 0.3 |
| Wasabi japonica | 2.8 |
| Olive leaf | 1.8 |
| Theacrine | 1.3 |
| Copper Niacin Complex | 0.00008 |

Table 6 below shows an example embodiment of the composition.

TABLE 6

| Component | Weight Percent in Blend |
|---|---|
| Acetyl-L-Carnitine | 15.3 |
| Quercetin | 1.2 |
| Grape | 0.3 |
| Lipoic acid | 0.2 |
| Coenzyme Q10 | 0.06 |
| Milk Thistle | 3.7 |
| Ashwagandha | 1.6 |
| Bacopa monnieri | 1.6 |
| Green Tea | 0.4 |
| Turmeric | 0.4 |
| Wasabi japonica | 3.7 |
| Olive leaf | 2.4 |
| Theacrine | 1.7 |
| Copper Niacin Complex | 0.0001 |

Table 7 below shows an example embodiment of the composition.

TABLE 7

| Component | Weight Percent in Blend |
|---|---|
| Acetyl-L-Carnitine | 12.8 |
| Quercetin | 3.6 |
| Grape | 1.8 |
| Lipoic acid | 1.3 |
| Coenzyme Q10 | 0.8 |
| Milk Thistle | 11.5 |

TABLE 7-continued

| Component | Weight Percent in Blend |
|---|---|
| Ashwagandha | 7.7 |
| Bacopa monnieri | 7.7 |
| Green Tea | 3.8 |
| Turmeric | 3.8 |
| Wasabi japonica | 5.1 |
| Olive leaf | 3.8 |
| Theacrine | 3.1 |
| Copper Niacin Complex | 0.1 |

Table 8 below shows an example embodiment of the composition.

TABLE 8

| Component | Weight Percent in Blend |
|---|---|
| Ashwagandha extract | 7.6 |
| Bacopa monnieri extract | 7.8 |
| Green tea extract | 3.9 |
| Turmeric extract | 3.9 |
| Acetyl-L-Carnitine | 26.0 |
| Quercetin | 7.3 |
| Grape extract | 3.6 |
| Lipoic acid | 2.6 |
| Coenzyme Q10 | 1.6 |
| Olive leaf extract | 6.5 |
| Alpinia galanga | 9.4 |
| Wasabi japonica powder | 8.0 |
| Nicotinic acid | 0.1 |
| Milk Thistle Extract | 11.7 |

Table 9 below shows an example embodiment of the composition.

TABLE 9

| Component | Weight Percent Total Composition |
|---|---|
| Milk thistle extract | 11.5 |
| Ashwagandha extract | 7.7 |
| Bacopa monnieri extract | 7.7 |
| Green tea extract | 3.8 |
| Turmeric extract | 3.8 |
| Hydroxypropyl methylcellulose | 0.5 |
| Calcium | 7.9 |
| Calcium carbonate gran | 6.1 |
| Microcrystalline cellulose | 5.1 |
| Croscarmellose sodium | 1.5 |
| Silica | 0.5 |
| Medium chain triglycerides | 0.5 |
| Magnesium | 0.7 |
| Purified water | 3.8 |
| Acetyl-L-carnitine | 12.8 |
| Quercetin | 3.6 |
| Lipoic acid | 1.3 |
| Coenzyme Q10 | 0.8 |
| Grape extract | 1.8 |
| Wasabi rhizome powder | 5.0 |
| Alpinia galanga | 4.5 |
| Nicotinic acid | 0.1 |
| Olive extract | 2.5 |
| Rice flour | 6.3 |
| Syloid | 0.2 |

Table 10 below shows an example embodiment of the composition.

TABLE 10

| Component | Weight Percent in Blend |
|---|---|
| Acetyl-L-Carnitine | 32.9 |
| Quercetin | 3.2 |
| Grape | 2.3 |
| Lipoic acid | 0.3 |
| Coenzyme Q10 | 0.1 |
| Milk Thistle | 8.5 |
| Ashwagandha | 4.2 |
| Bacopa monnieri | 4.8 |
| Green Tea | 13.5 |
| Turmeric | 8.6 |
| Wasabi japonica | 8.4 |
| Olive leaf | 7.5 |
| Alpinia galanga | 5.7 |
| Nicotinic acid | 0.0002 |

Table 11 below shows an example embodiment of the composition.

TABLE 11

| Component | Weight Percent in Blend |
|---|---|
| Acetyl-L-Carnitine | 12.2 |
| Quercetin | 0.2 |
| Grape | 0.04 |
| Lipoic acid | 0.02 |
| Coenzyme Q10 | 0.008 |
| Milk Thistle | 0.5 |
| Ashwagandha | 0.2 |
| Bacopa monnieri | 0.2 |
| Green Tea | 0.05 |
| Turmeric | 0.05 |
| Wasabi japonica | 0.3 |
| Olive leaf | 0.2 |
| Alpinia galanga | 1.2 |
| Nicotinic acid | 0.000008 |

Table 12 below shows an example embodiment of the composition.

TABLE 12

| Component | Weight Percent in Blend |
|---|---|
| Acetyl-L-Carnitine | 12.3 |
| Quercetin | 1.0 |
| Grape | 0.2 |
| Lipoic acid | 0.1 |
| Coenzyme Q10 | 0.04 |
| Milk Thistle | 2.9 |
| Ashwagandha | 1.3 |
| Bacopa monnieri | 1.2 |
| Green Tea | 5.6 |
| Turmeric | 0.3 |
| Wasabi japonica | 2.8 |
| Olive leaf | 3.5 |
| Alpinia galanga | 2.4 |
| Nicotinic acid | 0.00008 |

Table 13 below shows an example embodiment of the composition.

TABLE 13

| Component | Weight Percent in Blend |
|---|---|
| Acetyl-L-Carnitine | 15.3 |
| Quercetin | 1.2 |
| Grape | 0.3 |
| Lipoic acid | 0.2 |
| Coenzyme Q10 | 0.06 |
| Milk Thistle | 3.7 |
| Ashwagandha | 1.6 |
| Bacopa monnieri | 1.6 |
| Green Tea | 0.4 |
| Turmeric | 0.4 |
| Wasabi japonica | 3.7 |
| Olive leaf | 2.4 |
| Alpinia galanga | 2.4 |
| Nicotinic acid | 0.0001 |

Table 14 below shows an example embodiment of the composition.

TABLE 14

| Component | Weight Percent in Blend |
|---|---|
| Acetyl-L-Carnitine | 12.8 |
| Quercetin | 3.6 |
| Grape | 1.8 |
| Lipoic acid | 1.3 |
| Coenzyme Q10 | 0.8 |
| Milk Thistle | 11.5 |
| Ashwagandha | 7.1 |
| Bacopa monnieri | 7.7 |
| Green Tea | 3.8 |
| Turmeric | 3.8 |
| Wasabi japonica | 5.1 |
| Olive leaf | 3.8 |
| Alpinia galanga | 4.2 |
| Nicotinic acid | 0.1 |

Table 15 below shows an example embodiment of the composition.

TABLE 15

| Component | Weight Percent in Blend |
|---|---|
| Ashwagandha extract | 7.6 |
| Bacopa monnieri extract | 7.8 |
| Green tea extract | 3.9 |
| Turmeric extract | 3.9 |
| Acetyl-L-Carnitine | 26.0 |
| Quercetin | 7.3 |
| Grape extract | 3.6 |
| Lipoic acid | 2.6 |
| Coenzyme Q10 | 1.6 |
| Olive leaf extract | 6.5 |
| Capsaicin | 2.3 |
| Wasabi japonica powder | 8.0 |
| Nicotinic acid | 0.1 |
| Milk Thistle Extract | 11.7 |
| Copper gluconate | 0.1 |

Table 16 below shows an example embodiment of the composition.

TABLE 16

| Component | Weight Percent Total Composition |
|---|---|
| Milk thistle extract | 11.5 |
| Ashwagandha extract | 7.7 |
| Bacopa monnieri extract | 7.7 |
| Green tea extract | 3.8 |
| Turmeric extract | 3.8 |
| Hydroxypropyl methylcellulose | 0.5 |
| Calcium | 7.9 |
| Calcium carbonate gran | 6.1 |
| Microcrystalline cellulose | 5.1 |
| Croscarmellose sodium | 1.5 |
| Silica | 0.5 |
| Medium chain triglycerides | 0.5 |
| Magnesium | 0.7 |
| Purified water | 3.8 |
| Acetyl-L-carnitine | 12.8 |
| Quercetin | 3.6 |
| Lipoic acid | 1.3 |
| Coenzyme Q10 | 0.8 |
| Grape extract | 1.8 |
| Wasabi rhizome powder | 5.0 |
| Capsaicin | 2.3 |
| Nicotinic acid | 0.1 |
| Olive extract | 2.5 |
| Rice flour | 6.3 |
| Syloid | 0.2 |
| Copper gluconate | 0.01 |

Table 17 below shows an example embodiment of the composition.

TABLE 17

| Component | Weight Percent in Blend |
|---|---|
| Acetyl-L-Carnitine | 32.9 |
| Quercetin | 3.2 |
| Grape | 2.3 |
| Lipoic acid | 0.3 |
| Coenzyme Q10 | 0.1 |
| Milk Thistle | 8.5 |
| Ashwagandha | 4.2 |
| Bacopa monnieri | 4.8 |
| Green Tea | 13.5 |
| Turmeric | 8.6 |
| Wasabi japonica | 8.4 |
| Olive leaf | 7.5 |
| Capsaicin | 4.6 |
| Nicotinic acid | 0.0002 |

Table 18 below shows an example embodiment of the composition.

TABLE 18

| Component | Weight Percent in Blend |
|---|---|
| Acetyl-L-Carnitine | 12.2 |
| Quercetin | 0.2 |
| Grape | 0.04 |
| Lipoic acid | 0.02 |
| Coenzyme Q10 | 0.008 |
| Milk Thistle | 0.5 |
| Ashwagandha | 0.2 |
| Bacopa monnieri | 0.2 |
| Green Tea | 0.05 |
| Turmeric | 0.05 |
| Wasabi japonica | 0.3 |
| Olive leaf | 0.2 |

TABLE 18-continued

| Component | Weight Percent in Blend |
|---|---|
| Capsaicin | 0.8 |
| Nicotinic acid | 0.000008 |

Table 19 below shows an example embodiment of the composition.

TABLE 19

| Component | Weight Percent in Blend |
|---|---|
| Acetyl-L-Carnitine | 12.3 |
| Quercetin | 1.0 |
| Grape | 0.2 |
| Lipoic acid | 0.1 |
| Coenzyme Q10 | 0.04 |
| Milk Thistle | 2.9 |
| Ashwagandha | 1.3 |
| Bacopa monnieri | 1.2 |
| Green Tea | 5.6 |
| Turmeric | 0.3 |
| Wasabi japonica | 2.8 |
| Olive leaf | 3.5 |
| Capsaicin | 1.8 |
| Nicotinic acid | 0.00008 |

Table 20 below shows an example embodiment of the composition.

TABLE 20

| Component | Weight Percent in Blend |
|---|---|
| Acetyl-L-Carnitine | 15.3 |
| Quercetin | 1.2 |
| Grape | 0.3 |
| Lipoic acid | 0.2 |
| Coenzyme Q10 | 0.06 |
| Milk Thistle | 3.7 |
| Ashwagandha | 1.6 |
| Bacopa monnieri | 1.6 |
| Green Tea | 0.4 |
| Turmeric | 0.4 |
| Wasabi japonica | 3.7 |
| Olive leaf | 2.4 |
| Capsaicin | 2.4 |
| Nicotinic acid | 0.0001 |

Table 21 below shows an example embodiment of the composition.

TABLE 21

| Component | Weight Percent in Blend |
|---|---|
| Acetyl-L-Carnitine | 12.8 |
| Quercetin | 3.6 |
| Grape | 1.8 |
| Lipoic acid | 1.3 |
| Coenzyme Q10 | 0.8 |
| Milk Thistle | 11.5 |
| Ashwagandha | 7.1 |
| Bacopa monnieri | 7.7 |
| Green Tea | 3.8 |
| Turmeric | 3.8 |
| Wasabi japonica | 5.1 |
| Olive leaf | 3.8 |
| Capsaicin | 4.2 |
| Nicotinic acid | 0.1 |

Table 22 below shows an example embodiment of the composition.

TABLE 22

| Component | Weight Percent in Blend |
|---|---|
| Ashwagandha extract | 7.6 |
| Bacopa monnieri extract | 7.8 |
| Green tea extract | 3.9 |
| Turmeric extract | 3.9 |
| Acetyl-L-Carnitine | 26.0 |
| Quercetin | 7.3 |
| Grape extract | 3.6 |
| Lipoic acid | 2.6 |
| Coenzyme Q10 | 1.6 |
| Olive leaf extract | 6.5 |
| Mango leaf extract | 2.3 |
| Wasabi japonica powder | 8.0 |
| Nicotinic acid | 0.1 |
| Milk Thistle Extract | 11.7 |
| Copper gluconate | 0.1 |

Table 23 below shows an example embodiment of the composition.

TABLE 23

| Component | Weight Percent Total Composition |
|---|---|
| Milk thistle extract | 11.5 |
| Ashwagandha extract | 7.7 |
| Bacopa monnieri extract | 7.7 |
| Green tea extract | 3.8 |
| Turmeric extract | 3.8 |
| Hydroxypropyl methylcellulose | 0.5 |
| Calcium | 7.9 |
| Calcium carbonate gran | 6.1 |
| Microcrystalline cellulose | 5.1 |
| Croscarmellose sodium | 1.5 |
| Silica | 0.5 |
| Medium chain triglycerides | 0.5 |
| Magnesium | 0.7 |
| Purified water | 3.8 |
| Acetyl-l-carnitine | 12.8 |
| Quercetin | 3.6 |
| Lipoic acid | 1.3 |
| Coenzyme Q10 | 0.8 |
| Grape extract | 1.8 |
| Wasabi rhizome powder | 5.0 |
| Mango leaf extract | 2.3 |
| Nicotinic acid | 0.1 |
| Olive extract | 2.5 |
| Rice flour | 6.3 |
| Syloid | 0.2 |
| Copper gluconate | 0.01 |

Table 24 below shows an example embodiment of the composition.

TABLE 24

| Component | Weight Percent in Blend |
|---|---|
| Acetyl-L-Carnitine | 32.9 |
| Quercetin | 3.2 |
| Grape | 2.3 |
| Lipoic acid | 0.3 |
| Coenzyme Q10 | 0.1 |
| Milk Thistle | 8.5 |
| Ashwagandha | 4.2 |
| Bacopa monnieri | 4.8 |
| Green Tea | 13.5 |
| Turmeric | 8.6 |
| Wasabi japonica | 8.4 |
| Olive leaf | 7.5 |
| Mango leaf extract | 4.6 |
| Nicotinic acid | 0.0002 |

Table 25 below shows an example embodiment of the composition.

TABLE 25

| Component | Weight Percent in Blend |
|---|---|
| Acetyl-L-Carnitine | 12.2 |
| Quercetin | 0.2 |
| Grape | 0.04 |
| Lipoic acid | 0.02 |
| Coenzyme Q10 | 0.008 |
| Milk Thistle | 0.5 |
| Ashwagandha | 0.2 |
| Bacopa monnieri | 0.2 |
| Green Tea | 0.05 |
| Turmeric | 0.05 |
| Wasabi japonica | 0.3 |
| Olive leaf | 0.2 |
| Mango leaf extract | 0.8 |
| Nicotinic acid | 0.000008 |

Table 26 below shows an example embodiment of the composition.

TABLE 26

| Component | Weight Percent in Blend |
|---|---|
| Acetyl-L-Carnitine | 12.3 |
| Quercetin | 1.0 |
| Grape | 0.2 |
| Lipoic acid | 0.1 |
| Coenzyme Q10 | 0.04 |
| Milk Thistle | 2.9 |
| Ashwagandha | 1.3 |
| Bacopa monnieri | 1.2 |
| Green Tea | 5.6 |
| Turmeric | 0.3 |
| Wasabi japonica | 2.8 |
| Olive leaf | 3.5 |
| Mango leaf extract | 1.8 |
| Nicotinic acid | 0.00008 |

Table 27 below shows an example embodiment of the composition.

TABLE 27

| Component | Weight Percent in Blend |
|---|---|
| Acetyl-L-Carnitine | 15.3 |
| Quercetin | 1.2 |
| Grape | 0.3 |
| Lipoic acid | 0.2 |
| Coenzyme Q10 | 0.06 |
| Milk Thistle | 3.7 |
| Ashwagandha | 1.6 |
| Bacopa monnieri | 1.6 |
| Green Tea | 0.4 |
| Turmeric | 0.4 |
| Wasabi japonica | 3.7 |
| Olive leaf | 2.4 |

TABLE 27-continued

| Component | Weight Percent in Blend |
|---|---|
| Mango leaf extract | 2.4 |
| Nicotinic acid | 0.0001 |

Table 28 below shows an example embodiment of the composition.

TABLE 28

| Component | Weight Percent in Blend |
|---|---|
| Acetyl-L-Carnitine | 12.8 |
| Quercetin | 3.6 |
| Grape | 1.8 |
| Lipoic acid | 1.3 |
| Coenzyme Q10 | 0.8 |
| Milk Thistle | 11.5 |
| Ashwagandha | 7.1 |
| Bacopa monnieri | 7.7 |
| Green Tea | 3.8 |
| Turmeric | 3.8 |
| Wasabi japonica | 5.1 |
| Olive leaf | 3.8 |
| Mango leaf extract | 4.2 |
| Nicotinic acid | 0.1 |

According to one or more embodiments of the disclosure, a composition may include a combination of all or some, but not all, of the following ingredients:
   a. acetyl-L-carnitine;
   b. coenzyme Q10;
   c. grape extract;
   d. lipoic acid;
   e. quercetin;
   f. calcium;
   g. milk thistle, may include milk thistle extract;
   h. alpinia galanga;
   i. capsaicin;
   j. mango leaf extract;
   k. bacopa, may include bacopa extract;
   l. ashwagandha, may include ashwagandha extract;
   m. green tea, may include green tea extract;
   n. onion, may include onion extract or onion powder;
   o. turmeric, may include turmeric extract;
   p. niacin, may specifically include cuprous niacin;
   q. copper;
   r. wasabi, may include wasabi powder;
   s. olive leaf, may include olive leaf extract;
   t. theacrine;
   u. ubiquinone;
   v. thionic acid;
   w. flavonoids;
   x. alkaline earth metals;
   y. isothiocyanates;
   z. grape (seed, pulp, skin);
   aa. calcium;
   bb. magnesium;
   cc. copper niacin complex;
   dd. proanthocyanins;
   ee. resveratrol;
   ff. garlic, may include garlic extract;
   gg. cinnamon, may include cinnamon extract or ground cinnamon powder;
   hh. caffeine;
   ii. theobromine;
   jj. yerba mate extracts;
   kk. cocoa, may include cocoa extract or ground cocoa powder;
   ll. ferulic acid;
   mm. rhubarb, may include rhubarb extract;
   nn. hydroxycinnamic acid;
   oo. ginger, may include ginger extract;
   pp. ginseng, may include ginseng extract;
   qq. skullcap;
   rr. Brazilian green propolis extract;
   ss. myricetin;
   tt. nicotinic acid;
   uu. nicotinamide;
   vv. nicotinamide c;
   ww. ribose;
   xx. vitamin B3;
   yy. nicotinamide mononucleotide;
   zz. tryptophan;
   aaa. quinolinic acid;
   bbb. beta-namn; and/or
   ccc. beta-naad.

Embodiments of the composition may comprise, for example, concentrations of acetyl-L-carnitine as follows:
   a1) from about 2 wt % to about 90 wt % the total composition;
   a2) from about 5 wt % to about 90 wt % the total composition;
   a3) from about 10 wt % to about 90 wt % the total composition;
   a4) from about 15 wt % to about 90 wt % the total composition;
   a5) from about 20 wt % to about 90 wt % the total composition;
   a6) from about 25 wt % to about 90 wt % the total composition;
   a7) from about 30 wt % to about 90 wt % the total composition;
   a8) from about 2 wt % to about 85 wt % the total composition;
   a9) from about 2 wt % to about 80 wt % the total composition;
   a10) from about 2 wt % to about 75 wt % the total composition;
   a11) from about 2 wt % to about 70 wt % the total composition;
   a12) from about 2 wt % to about 65 wt % the total composition;
   a13) from about 2 wt % to about 50 wt % the total composition;
   a14) from about 2 wt % to about 45 wt % the total composition;
   a15) from about 2 wt % to about 40 wt % the total composition;
   a16) from about 2 wt % to about 35 wt % the total composition;
   a17) from about 2 wt % to about 30 wt % the total composition;
   a18) from about 2 wt % to about 25 wt % the total composition;
   a19) from about 2 wt % to about 20 wt % the total composition;
   a20) from about 2 wt % to about 15 wt % the total composition;
   a21) from about 2 wt % to about 10 wt % the total composition;
   a22) from about 20 wt % to about 30 wt % the total composition;

a23) from about 22 wt % to about 30 wt % the total composition;
a24) from about 24 wt % to about 30 wt % the total composition;
a25) from about 25 wt % to about 30 wt % the total composition;
a26) from about 26 wt % to about 30 wt % the total composition;
a27) from about 28 wt % to about 30 wt % the total composition;
a28) from about 20 wt % to about 28 wt % the total composition;
a29) from about 20 wt % to about 26 wt % the total composition;
a30) from about 20 wt % to about 24 wt % the total composition;
a31) from about 10 wt % to about 30 wt % the total composition;
a32) from about 5 wt % to about 15 wt % the total composition;
a33) from about 5 wt % to about 14 wt % the total composition;
a34) from about 5 wt % to about 16 wt % the total composition;
a35) from about 5 wt % to about 18 wt % the total composition;
a36) from about 5 wt % to about 20 wt % the total composition;
a37) from about 10 wt % to about 13 wt % the total composition;
a38) from about 10 wt % to about 15 wt % the total composition;
a39) from about 5 wt % to about 40 wt % the total composition;
a40) from about 5 wt % to about 50 wt % the total composition; or
a41) from about 25 wt % to about 27 wt % the total composition.

Embodiments of the composition may comprise, for example, concentrations of coenzyme Q10 as follows:
b1) from about 0.005 wt % to about 50 wt % the total composition;
b2) from about 0.005 wt % to about 45 wt % the total composition;
b3) from about 0.005 wt % to about 40 wt % the total composition;
b4) from about 0.005 wt % to about 35 wt % the total composition;
b5) from about 0.005 wt % to about 30 wt % the total composition;
b6) from about 0.005 wt % to about 25 wt % the total composition;
b7) from about 0.005 wt % to about 20 wt % the total composition;
b8) from about 0.005 wt % to about 15 wt % the total composition;
b9) from about 0.005 wt % to about 10 wt % the total composition;
b10) from about 0.005 wt % to about 5 wt % the total composition;
b11) from about 0.005 wt % to about 4 wt % the total composition;
b12) from about 0.005 wt % to about 3 wt % the total composition;
b13) from about 0.005 wt % to about 2 wt % the total composition;
b14) from about 0.005 wt % to about 1 wt % the total composition;
b15) from about 0.005 wt % to about 0.9 wt % the total composition;
b16) from about 0.005 wt % to about 0.8 wt % the total composition;
b17) from about 0.005 wt % to about 0.7 wt % the total composition;
b18) from about 0.005 wt % to about 0.6 wt % the total composition;
b19) from about 0.005 wt % to about 0.5 wt % the total composition;
b20) from about 0.005 wt % to about 0.4 wt % the total composition;
b21) from about 0.005 wt % to about 0.3 wt % the total composition;
b22) from about 0.005 wt % to about 0.2 wt % the total composition;
b23) from about 0.005 wt % to about 0.1 wt % the total composition;
b24) from about 0.008 wt % to about 1 wt % the total composition;
b25) from about 0.008 wt % to about 0.9 wt % the total composition;
b26) from about 0.008 wt % to about 0.8 wt % the total composition;
b27) from about 0.008 wt % to about 0.7 wt % the total composition;
b28) from about 0.008 wt % to about 0.6 wt % the total composition;
b29) from about 0.008 wt % to about 0.5 wt % the total composition;
b30) from about 0.008 wt % to about 0.4 wt % the total composition;
b31) from about 0.008 wt % to about 0.3 wt % the total composition;
b32) from about 0.5 wt % to about 5 wt % the total composition;
b33) from about 1 wt % to about 5 wt % the total composition;
b34) from about 2 wt % to about 5 wt % the total composition;
b35) from about 3 wt % to about 5 wt % the total composition;
b36) from about 4 wt % to about 5 wt % the total composition;
b37) from about 0.5 wt % to about 4 wt % the total composition;
b38) from about 0.5 wt % to about 3 wt % the total composition;
b39) from about 0.5 wt % to about 2 wt % the total composition;
b40) from about 0.5 wt % to about 6 wt % the total composition;
b41) from about 0.5 wt % to about 7 wt % the total composition;
b42) from about 0.5 wt % to about 8 wt % the total composition;
b43) from about 0.5 wt % to about 9 wt % the total composition;
b44) from about 0.5 wt % to about 10 wt % the total composition;
b45) from about 0.2 wt % to about 1 wt % the total composition;
b46) from about 0.3 wt % to about 1 wt % the total composition;

b47) from about 0.4 wt % to about 1 wt % the total composition; or b48) from about 0.6 wt % to about 0.9 wt % the total composition.

Embodiments of the composition may comprise, for example, concentrations of grape extract, which may include grape leaf extract, as follows:

c1) from about 0.04 wt % to about 20 wt % the total composition;

c2) from about 0.04 wt % to about 15 wt % the total composition;

c3) from about 0.04 wt % to about 10 wt % the total composition;

c4) from about 0.04 wt % to about 9 wt % the total composition;

c5) from about 0.04 wt % to about 8 wt % the total composition;

c6) from about 0.04 wt % to about 7 wt % the total composition;

c7) from about 0.04 wt % to about 6 wt % the total composition;

c8) from about 0.04 wt % to about 5 wt % the total composition;

c9) from about 0.04 wt % to about 4 wt % the total composition;

c10) from about 0.04 wt % to about 3 wt % the total composition;

c11) from about 0.04 wt % to about 2 wt % the total composition; or c12) from about 0.04 wt % to about 1 wt % the total composition.

Embodiments of the composition may comprise, for example, concentrations of lipoic acid as follows:

d1) from about 0.5 wt % to about 5 wt % the total composition;

d2) from about 1 wt % to about 5 wt % the total composition;

d3) from about 2 wt % to about 5 wt % the total composition;

d4) from about 3 wt % to about 5 wt % the total composition;

d5) from about 4 wt % to about 5 wt % the total composition;

d6) from about 0.5 wt % to about 4 wt % the total composition;

d7) from about 0.5 wt % to about 3 wt % the total composition;

d8) from about 0.5 wt % to about 2 wt % the total composition;

d9) from about 0.5 wt % to about 6 wt % the total composition;

d10) from about 0.5 wt % to about 7 wt % the total composition;

d11) from about 0.5 wt % to about 8 wt % the total composition;

d12) from about 0.5 wt % to about 9 wt % the total composition;

d13) from about 0.5 wt % to about 10 wt % the total composition;

d14) from about 2 wt % to about 3 wt % the total composition;

d15) from about 1 wt % to about 2 wt % the total composition;

d16) from about 1 wt % to about 1.5 wt % the total composition;

d17) from about 0.1 wt % to about 2 wt % the total composition; or d18) from about 0.1 wt % to about 4 wt % the total composition.

Embodiments of the composition may comprise, for example, concentrations of quercetin as follows:

e1) from about 0.1 wt % to about 40 wt % the total composition;

e2) from about 0.1 wt % to about 35 wt % the total composition;

e3) from about 0.1 wt % to about 30 wt % the total composition;

e4) from about 0.1 wt % to about 25 wt % the total composition;

e5) from about 0.1 wt % to about 20 wt % the total composition;

e6) from about 0.1 wt % to about 15 wt % the total composition;

e7) from about 0.1 wt % to about 10 wt % the total composition;

e8) from about 0.1 wt % to about 9 wt % the total composition;

e9) from about 0.1 wt % to about 8 wt % the total composition;

e10) from about 0.1 wt % to about 7 wt % the total composition;

e11) from about 0.1 wt % to about 6 wt % the total composition;

e12) from about 0.2 wt % to about 7 wt % the total composition;

e13) from about 0.3 wt % to about 7 wt % the total composition;

e14) from about 0.4 wt % to about 7 wt % the total composition;

e15) from about 0.5 wt % to about 7 wt % the total composition;

e16) from about 0.6 wt % to about 7 wt % the total composition;

e17) from about 0.7 wt % to about 7 wt % the total composition;

e18) from about 0.8 wt % to about 7 wt % the total composition;

e19) from about 0.9 wt % to about 7 wt % the total composition; or e20) from about 1 wt % to about 10 wt % the total composition.

Embodiments of the composition may comprise, for example, concentrations of alpinia galanga as follows:

h1) from about 0.1 wt % to about 55 wt % the total composition;

h2) from about 0.1 wt % to about 50 wt % the total composition;

h3) from about 0.1 wt % to about 45 wt % the total composition;

h4) from about 0.1 wt % to about 40 wt % the total composition;

h5) from about 0.1 wt % to about 35 wt % the total composition;

h6) from about 0.1 wt % to about 30 wt % the total composition;

h7) from about 0.1 wt % to about 25 wt % the total composition;

h8) from about 0.1 wt % to about 20 wt % the total composition;

h9) from about 0.1 wt % to about 15 wt % the total composition;

h10) from about 0.2 wt % to about 15 wt % the total composition;

h11) from about 0.3 wt % to about 15 wt % the total composition;
h12) from about 0.4 wt % to about 15 wt % the total composition;
h13) from about 0.5 wt % to about 15 wt % the total composition;
h14) from about 0.6 wt % to about 15 wt % the total composition;
h15) from about 0.7 wt % to about 15 wt % the total composition;
h16) from about 0.8 wt % to about 15 wt % the total composition;
h17) from about 0.9 wt % to about 15 wt % the total composition;
h18) from about 1 wt % to about 15 wt % the total composition;
h19) from about 2 wt % to about 15 wt % the total composition;
h20) from about 3 wt % to about 15 wt % the total composition;
h21) from about 4 wt % to about 15 wt % the total composition;
h22) from about 5 wt % to about 15 wt % the total composition;
h23) from about 6 wt % to about 15 wt % the total composition;
h24) from about 7 wt % to about 15 wt % the total composition;
h25) from about 8 wt % to about 15 wt % the total composition;
h26) from about 9 wt % to about 15 wt % the total composition;
h27) from about 10 wt % to about 15 wt % the total composition;
h28) from about 0.5 wt % to about 10 wt % the total composition;
h29) from about 1 wt % to about 10 wt % the total composition;
h30) from about 2 wt % to about 10 wt % the total composition;
h31) from about 3 wt % to about 10 wt % the total composition;
h32) from about 4 wt % to about 10 wt % the total composition;
h33) from about 5 wt % to about 10 wt % the total composition;
h34) from about 5 wt % to about 9 wt % the total composition;
h35) from about 5 wt % to about 8 wt % the total composition;
h36) from about 5 wt % to about 7 wt % the total composition;
h37) from about 5 wt % to about 6 wt % the total composition;
h38) from about 7 wt % to about 8 wt % the total composition;
h39) from about 6 wt % to about 9 wt % the total composition;
h40) from about 6 wt % to about 8 wt % the total composition;
h41) from about 5 wt % to about 15 wt % the total composition;
h42) from about 5 wt % to about 20 wt % the total composition;
h43) from about 2 wt % to about 4 wt % the total composition;
h44) from about 1 wt % to about 5 wt % the total composition;
h45) from about 1 wt % to about 8 wt % the total composition; or
h46) from about 1 wt % to about 10 wt % the total composition.

Embodiments of the composition may comprise, for example, concentrations of capsaicin as follows:
i1) from about 0.1 wt % to about 55 wt % the total composition;
i2) from about 0.1 wt % to about 50 wt % the total composition;
i3) from about 0.1 wt % to about 45 wt % the total composition;
i4) from about 0.1 wt % to about 40 wt % the total composition;
i5) from about 0.1 wt % to about 35 wt % the total composition;
i6) from about 0.1 wt % to about 30 wt % the total composition;
i7) from about 0.1 wt % to about 25 wt % the total composition;
i8) from about 0.1 wt % to about 20 wt % the total composition;
i9) from about 0.1 wt % to about 15 wt % the total composition;
i10) from about 0.2 wt % to about 15 wt % the total composition;
i11) from about 0.3 wt % to about 15 wt % the total composition;
i12) from about 0.4 wt % to about 15 wt % the total composition;
i13) from about 0.5 wt % to about 15 wt % the total composition;
i14) from about 0.6 wt % to about 15 wt % the total composition;
i15) from about 0.7 wt % to about 15 wt % the total composition;
i16) from about 0.8 wt % to about 15 wt % the total composition;
i17) from about 0.9 wt % to about 15 wt % the total composition;
i18) from about 1 wt % to about 15 wt % the total composition;
i19) from about 2 wt % to about 15 wt % the total composition;
i20) from about 3 wt % to about 15 wt % the total composition;
i21) from about 4 wt % to about 15 wt % the total composition;
i22) from about 5 wt % to about 15 wt % the total composition;
i23) from about 6 wt % to about 15 wt % the total composition;
i24) from about 7 wt % to about 15 wt % the total composition;
i25) from about 8 wt % to about 15 wt % the total composition;
i26) from about 9 wt % to about 15 wt % the total composition;
i27) from about 10 wt % to about 15 wt % the total composition;
i28) from about 0.5 wt % to about 10 wt % the total composition;
i29) from about 1 wt % to about 10 wt % the total composition;

i30) from about 2 wt % to about 10 wt % the total composition;
i31) from about 3 wt % to about 10 wt % the total composition;
i32) from about 4 wt % to about 10 wt % the total composition;
i33) from about 5 wt % to about 10 wt % the total composition;
i34) from about 5 wt % to about 9 wt % the total composition;
i35) from about 5 wt % to about 8 wt % the total composition;
i36) from about 5 wt % to about 7 wt % the total composition;
i37) from about 5 wt % to about 6 wt % the total composition;
i38) from about 7 wt % to about 8 wt % the total composition;
i39) from about 6 wt % to about 9 wt % the total composition;
i40) from about 6 wt % to about 8 wt % the total composition;
i41) from about 5 wt % to about 15 wt % the total composition;
i42) from about 5 wt % to about 20 wt % the total composition;
i43) from about 2 wt % to about 4 wt % the total composition;
i44) from about 1 wt % to about 5 wt % the total composition;
i45) from about 1 wt % to about 8 wt % the total composition; or
i46) from about 1 wt % to about 10 wt % the total composition.

Embodiments of the composition may comprise, for example, concentrations of mango leaf extract as follows:
j1) from about 0.1 wt % to about 55 wt % the total composition;
j2) from about 0.1 wt % to about 50 wt % the total composition;
j3) from about 0.1 wt % to about 45 wt % the total composition;
j4) from about 0.1 wt % to about 40 wt % the total composition;
j5) from about 0.1 wt % to about 35 wt % the total composition;
j6) from about 0.1 wt % to about 30 wt % the total composition;
j7) from about 0.1 wt % to about 25 wt % the total composition;
j8) from about 0.1 wt % to about 20 wt % the total composition;
j9) from about 0.1 wt % to about 15 wt % the total composition;
j10) from about 0.2 wt % to about 15 wt % the total composition;
j11) from about 0.3 wt % to about 15 wt % the total composition;
j12) from about 0.4 wt % to about 15 wt % the total composition;
j13) from about 0.5 wt % to about 15 wt % the total composition;
j14) from about 0.6 wt % to about 15 wt % the total composition;
j15) from about 0.7 wt % to about 15 wt % the total composition;
j16) from about 0.8 wt % to about 15 wt % the total composition;
j17) from about 0.9 wt % to about 15 wt % the total composition;
j18) from about 1 wt % to about 15 wt % the total composition;
j19) from about 2 wt % to about 15 wt % the total composition;
j20) from about 3 wt % to about 15 wt % the total composition;
j21) from about 4 wt % to about 15 wt % the total composition;
j22) from about 5 wt % to about 15 wt % the total composition;
j23) from about 6 wt % to about 15 wt % the total composition;
j24) from about 7 wt % to about 15 wt % the total composition;
j25) from about 8 wt % to about 15 wt % the total composition;
j26) from about 9 wt % to about 15 wt % the total composition;
j27) from about 10 wt % to about 15 wt % the total composition;
j28) from about 0.5 wt % to about 10 wt % the total composition;
j29) from about 1 wt % to about 10 wt % the total composition;
j30) from about 2 wt % to about 10 wt % the total composition;
j31) from about 3 wt % to about 10 wt % the total composition;
j32) from about 4 wt % to about 10 wt % the total composition;
j33) from about 5 wt % to about 10 wt % the total composition;
j34) from about 5 wt % to about 9 wt % the total composition;
j35) from about 5 wt % to about 8 wt % the total composition;
j36) from about 5 wt % to about 7 wt % the total composition;
j37) from about 5 wt % to about 6 wt % the total composition;
j38) from about 7 wt % to about 8 wt % the total composition;
j39) from about 6 wt % to about 9 wt % the total composition;
j40) from about 6 wt % to about 8 wt % the total composition;
j41) from about 5 wt % to about 15 wt % the total composition;
j42) from about 5 wt % to about 20 wt % the total composition;
j43) from about 2 wt % to about 4 wt % the total composition;
j44) from about 1 wt % to about 5 wt % the total composition;
j45) from about 1 wt % to about 8 wt % the total composition; or
j46) from about 1 wt % to about 10 wt % the total composition.

Embodiments of the composition may comprise, for example, concentrations of ashwagandha as follows:
l1) from about 0.2 wt % to about 60 wt % the total composition;

l2) from about 0.2 wt % to about 55 wt % the total composition;
l3) from about 0.2 wt % to about 50 wt % the total composition;
l4) from about 0.2 wt % to about 45 wt % the total composition;
l5) from about 0.2 wt % to about 40 wt % the total composition;
l6) from about 0.2 wt % to about 35 wt % the total composition;
l7) from about 0.2 wt % to about 30 wt % the total composition;
l8) from about 0.2 wt % to about 25 wt % the total composition;
l9) from about 0.2 wt % to about 20 wt % the total composition;
l10) from about 0.2 wt % to about 15 wt % the total composition;
l11) from about 0.2 wt % to about 10 wt % the total composition;
l12) from about 0.2 wt % to about 9 wt % the total composition;
l13) from about 0.2 wt % to about 8 wt % the total composition;
l14) from about 0.2 wt % to about 7 wt % the total composition;
l15) from about 0.2 wt % to about 6 wt % the total composition;
l16) from about 0.2 wt % to about 5 wt % the total composition;
l17) from about 0.2 wt % to about 4 wt % the total composition;
l18) from about 0.2 wt % to about 3 wt % the total composition;
l19) from about 0.2 wt % to about 15 wt % the total composition;
l20) from about 0.3 wt % to about 15 wt % the total composition;
l21) from about 0.4 wt % to about 15 wt % the total composition;
l22) from about 0.5 wt % to about 15 wt % the total composition;
l23) from about 0.6 wt % to about 15 wt % the total composition;
l24) from about 0.7 wt % to about 15 wt % the total composition;
l25) from about 0.8 wt % to about 15 wt % the total composition;
l26) from about 0.9 wt % to about 15 wt % the total composition;
l27) from about 1 wt % to about 15 wt % the total composition;
l28) from about 2 wt % to about 15 wt % the total composition;
l29) from about 3 wt % to about 15 wt % the total composition;
l30) from about 4 wt % to about 15 wt % the total composition;
l31) from about 5 wt % to about 15 wt % the total composition;
l32) from about 6 wt % to about 15 wt % the total composition;
l33) from about 7 wt % to about 15 wt % the total composition;
l34) from about 8 wt % to about 15 wt % the total composition;
l35) from about 9 wt % to about 15 wt % the total composition;
l36) from about 10 wt % to about 15 wt % the total composition;
l37) from about 11 wt % to about 15 wt % the total composition;
l38) from about 0.5 wt % to about 10 wt % the total composition;
l39) from about 1 wt % to about 10 wt % the total composition;
l40) from about 2 wt % to about 10 wt % the total composition;
l41) from about 3 wt % to about 10 wt % the total composition;
l42) from about 4 wt % to about 10 wt % the total composition;
l43) from about 5 wt % to about 10 wt % the total composition;
l44) from about 5 wt % to about 9 wt % the total composition;
l45) from about 5 wt % to about 8 wt % the total composition;
l46) from about 5 wt % to about 7 wt % the total composition;
l47) from about 5 wt % to about 6 wt % the total composition;
l48) from about 7 wt % to about 8 wt % the total composition;
l49) from about 6 wt % to about 9 wt % the total composition;
l50) from about 6 wt % to about 8 wt % the total composition;
l51) from about 5 wt % to about 15 wt % the total composition; or
l52) from about 5 wt % to about 20 wt % the total composition.

Other embodiments of the composition may comprise, for example, concentrations of green tea extract as follows:
m1) from about 0.05 wt % to about 40 wt % the total composition;
m2) from about 0.05 wt % to about 35 wt % the total composition;
m3) from about 0.05 wt % to about 30 wt % the total composition;
m4) from about 0.05 wt % to about 25 wt % the total composition;
m5) from about 0.05 wt % to about 20 wt % the total composition;
m6) from about 0.05 wt % to about 15 wt % the total composition;
m7) from about 0.05 wt % to about 10 wt % the total composition;
m8) from about 0.05 wt % to about 9 wt % the total composition;
m9) from about 0.05 wt % to about 8 wt % the total composition;
m10) from about 0.05 wt % to about 7 wt % the total composition;
m11) from about 0.05 wt % to about 6 wt % the total composition;
m12) from about 0.05 wt % to about 5 wt % the total composition;
m13) from about 0.05 wt % to about 4 wt % the total composition;
m14) from about 0.05 wt % to about 3 wt % the total composition;

m15) from about 0.05 wt % to about 2.5 wt % the total composition;
m16) from about 0.1 wt % to about 5 wt % the total composition;
m17) from about 0.2 wt % to about 5 wt % the total composition;
m18) from about 0.3 wt % to about 5 wt % the total composition;
m19) from about 0.4 wt % to about 5 wt % the total composition;
m20) from about 0.5 wt % to about 5 wt % the total composition;
m21) from about 0.7 wt % to about 5 wt % the total composition;
m22) from about 0.8 wt % to about 5 wt % the total composition;
m23) from about 0.9 wt % to about 5 wt % the total composition;
m24) from about 1 wt % to about 5 wt % the total composition;
m25) from about 1.1 wt % to about 5 wt % the total composition;
m26) from about 1.2 wt % to about 5 wt % the total composition;
m27) from about 1.3 wt % to about 5 wt % the total composition;
m28) from about 1.4 wt % to about 5 wt % the total composition;
m29) from about 1.5 wt % to about 5 wt % the total composition;
m30) from about 1.6 wt % to about 5 wt % the total composition;
m31) from about 1 wt % to about 5 wt % the total composition;
m32) from about 1 wt % to about 4 wt % the total composition;
m33) from about 1 wt % to about 3 wt % the total composition;
m34) from about 2 wt % to about 5 wt % the total composition;
m35) from about 3 wt % to about 5 wt % the total composition;
m36) from about 4 wt % to about 5 wt % the total composition;
m37) from about 3 wt % to about 6 wt % the total composition;
m38) from about 3 wt % to about 7 wt % the total composition;
m39) from about 3 wt % to about 8 wt % the total composition;
m40) from about 3 wt % to about 9 wt % the total composition;
m41) from about 3 wt % to about 10 wt % the total composition;
m42) from about 3 wt % to about 15 wt % the total composition;
m43) from about 3 wt % to about 20 wt % the total composition;
m44) from about 4 wt % to about 20 wt % the total composition;
m45) from about 5 wt % to about 20 wt % the total composition;
m46) from about 0.5 wt % to about 5 wt % the total composition;
m47) from about 0.5 wt % to about 6 wt % the total composition; or
m48) from about 0.5 wt % to about 8 wt % the total composition.

Embodiments of the composition may comprise, for example, concentrations of turmeric as follows:
o1) from about 2 wt % to about 5 wt % the total composition;
o2) from about 0.05 wt % to about 40 wt % the total composition;
o3) from about 0.05 wt % to about 35 wt % the total composition;
o4) from about 0.05 wt % to about 30 wt % the total composition;
o5) from about 0.05 wt % to about 25 wt % the total composition;
o6) from about 0.05 wt % to about 20 wt % the total composition;
o7) from about 0.05 wt % to about 15 wt % the total composition;
o8) from about 0.05 wt % to about 10 wt % the total composition;
o9) from about 0.05 wt % to about 9 wt % the total composition;
o10) from about 0.05 wt % to about 8 wt % the total composition;
o11) from about 0.05 wt % to about 7 wt % the total composition;
o12) from about 0.05 wt % to about 6 wt % the total composition;
o13) from about 0.05 wt % to about 5 wt % the total composition;
o14) from about 0.05 wt % to about 4 wt % the total composition;
o15) from about 0.05 wt % to about 3 wt % the total composition;
o16) from about 0.05 wt % to about 2.5 wt % the total composition;
o17) from about 0.1 wt % to about 5 wt % the total composition;
o18) from about 0.2 wt % to about 5 wt % the total composition;
o19) from about 0.3 wt % to about 5 wt % the total composition;
o20) from about 0.4 wt % to about 5 wt % the total composition;
o21) from about 0.5 wt % to about 5 wt % the total composition;
o22) from about 0.7 wt % to about 5 wt % the total composition;
o23) from about 0.8 wt % to about 5 wt % the total composition;
o24) from about 0.9 wt % to about 5 wt % the total composition;
o25) from about 1 wt % to about 5 wt % the total composition;
o26) from about 1.1 wt % to about 5 wt % the total composition;
o27) from about 1.2 wt % to about 5 wt % the total composition;
o28) from about 1.3 wt % to about 5 wt % the total composition;
o29) from about 1.4 wt % to about 5 wt % the total composition;
o30) from about 1.5 wt % to about 5 wt % the total composition;
o31) from about 1.6 wt % to about 5 wt % the total composition;

o32) from about 1 wt % to about 5 wt % the total composition;
o33) from about 1 wt % to about 4 wt % the total composition;
o34) from about 1 wt % to about 3 wt % the total composition;
o35) from about 3 wt % to about 5 wt % the total composition;
o36) from about 4 wt % to about 5 wt % the total composition;
o37) from about 3 wt % to about 6 wt % the total composition;
o38) from about 3 wt % to about 7 wt % the total composition;
o39) from about 3 wt % to about 8 wt % the total composition;
o40) from about 3 wt % to about 9 wt % the total composition;
o41) from about 3 wt % to about 10 wt % the total composition;
o42) from about 3 wt % to about 15 wt % the total composition;
o43) from about 3 wt % to about 20 wt % the total composition;
o44) from about 4 wt % to about 20 wt % the total composition;
o45) from about 5 wt % to about 20 wt % the total composition;
o46) from about 0.5 wt % to about 5 wt % the total composition;
o47) from about 0.5 wt % to about 6 wt % the total composition; or
o48) from about 0.5 wt % to about 8 wt % the total composition.

Embodiments of the disclosure may comprise, for example, concentrations of niacin as follows:
p1) from about 0 wt % to about 5 wt % the total composition;
p2) from about 0.0001 wt % to about 5 wt % the total composition;
p3) from about 0.0001 wt % to about 4 wt % the total composition;
p4) from about 0.0001 wt % to about 3 wt % the total composition;
p5) from about 0.0001 wt % to about 2 wt % the total composition;
p6) from about 0.0001 wt % to about 1 wt % the total composition;
p7) from about 0.0001 wt % to about 0.9 wt % the total composition;
p8) from about 0.0001 wt % to about 0.8 wt % the total composition;
p9) from about 0.0001 wt % to about 0.7 wt % the total composition;
p10) from about 0.0001 wt % to about 0.6 wt % the total composition;
p11) from about 0.0001 wt % to about 0.5 wt % the total composition;
p12) from about 0.0001 wt % to about 0.4 wt % the total composition;
p13) from about 0.0001 wt % to about 0.3 wt % the total composition;
p14) from about 0.0001 wt % to about 0.2 wt % the total composition;
p15) from about 0.0001 wt % to about 0.1 wt % the total composition; or
p16) from about 0.0001 wt % to about 0.001 wt % the total composition.

Embodiments of the disclosure may comprise, for example, concentrations of wasabi as follows:
r1) from about 0.3 wt % to about 70 wt % the total composition;
r2) from about 0.3 wt % to about 65 wt % the total composition;
r3) from about 0.3 wt % to about 60 wt % the total composition;
r4) from about 0.3 wt % to about 55 wt % the total composition;
r5) from about 0.3 wt % to about 55 wt % the total composition;
r6) from about 0.3 wt % to about 40 wt % the total composition;
r7) from about 0.3 wt % to about 35 wt % the total composition;
r8) from about 0.4 wt % to about 35 wt % the total composition;
r9) from about 0.5 wt % to about 35 wt % the total composition;
r10) from about 0.6 wt % to about 35 wt % the total composition;
r11) from about 0.7 wt % to about 35 wt % the total composition;
r12) from about 0.8 wt % to about 35 wt % the total composition;
r13) from about 0.9 wt % to about 35 wt % the total composition;
r14) from about 1 wt % to about 35 wt % the total composition;
r15) from about 5 wt % to about 35 wt % the total composition;
r16) from about 10 wt % to about 35 wt % the total composition;
r17) from about 15 wt % to about 35 wt % the total composition;
r18) from about 0.5 wt % to about 10 wt % the total composition;
r19) from about 1 wt % to about 10 wt % the total composition;
r20) from about 2 wt % to about 10 wt % the total composition;
r21) from about 3 wt % to about 10 wt % the total composition;
r22) from about 4 wt % to about 10 wt % the total composition;
r23) from about 5 wt % to about 10 wt % the total composition;
r24) from about 5 wt % to about 9 wt % the total composition;
r25) from about 5 wt % to about 8 wt % the total composition;
r26) from about 5 wt % to about 7 wt % the total composition;
r27) from about 5 wt % to about 6 wt % the total composition;
r28) from about 7 wt % to about 8 wt % the total composition;
r29) from about 6 wt % to about 9 wt % the total composition;
r30) from about 6 wt % to about 8 wt % the total composition; or
r31) from about 5 wt % to about 15 wt % the total composition.

Embodiments of the composition may comprise, for example, concentrations of olive leaf as follows:

s1) from about 0.2 wt % to about 60 wt % the total composition;
s2) from about 0.2 wt % to about 55 wt % the total composition;
s3) from about 0.2 wt % to about 50 wt % the total composition;
s4) from about 0.2 wt % to about 45 wt % the total composition;
s5) from about 0.2 wt % to about 40 wt % the total composition;
s6) from about 0.2 wt % to about 35 wt % the total composition;
s7) from about 0.2 wt % to about 30 wt % the total composition;
s8) from about 0.2 wt % to about 25 wt % the total composition;
s9) from about 0.2 wt % to about 24 wt % the total composition;
s10) from about 0.2 wt % to about 23 wt % the total composition;
s11) from about 0.2 wt % to about 22 wt % the total composition;
s12) from about 0.3 wt % to about 23 wt % the total composition;
s13) from about 0.4 wt % to about 23 wt % the total composition;
s14) from about 0.5 wt % to about 23 wt % the total composition;
s15) from about 0.6 wt % to about 23 wt % the total composition;
s16) from about 0.7 wt % to about 23 wt % the total composition;
s17) from about 0.8 wt % to about 23 wt % the total composition;
s18) from about 0.9 wt % to about 23 wt % the total composition;
s19) from about 1 wt % to about 23 wt % the total composition;
s20) from about 2 wt % to about 23 wt % the total composition;
s21) from about 3 wt % to about 23 wt % the total composition;
s22) from about 4 wt % to about 23 wt % the total composition;
s23) from about 5 wt % to about 23 wt % the total composition;
s24) from about 10 wt % to about 23 wt % the total composition;
s25) from about 15 wt % to about 23 wt % the total composition;
s26) from about 0.5 wt % to about 10 wt % the total composition;
s27) from about 1 wt % to about 10 wt % the total composition;
s28) from about 2 wt % to about 10 wt % the total composition;
s29) from about 3 wt % to about 10 wt % the total composition;
s30) from about 4 wt % to about 10 wt % the total composition;
s31) from about 5 wt % to about 10 wt % the total composition;
s32) from about 5 wt % to about 9 wt % the total composition;
s33) from about 5 wt % to about 8 wt % the total composition;
s34) from about 5 wt % to about 7 wt % the total composition;
s35) from about 5 wt % to about 6 wt % the total composition;
s36) from about 7 wt % to about 8 wt % the total composition;
s37) from about 6 wt % to about 9 wt % the total composition;
s38) from about 6 wt % to about 8 wt % the total composition;
s39) from about 5 wt % to about 15 wt % the total composition;
s40) from about 5 wt % to about 20 wt % the total composition;
s41) from about 2 wt % to about 6 wt % the total composition;
s42) from about 1 wt % to about 6 wt % the total composition; or
s43) from about 2 wt % to about 4 wt % the total composition.

Embodiments of the composition may comprise, for example, concentrations of theacrine as follows:

t1) from about 0.1 wt % to about 55 wt % the total composition;
t2) from about 0.1 wt % to about 50 wt % the total composition;
t3) from about 0.1 wt % to about 45 wt % the total composition;
t4) from about 0.1 wt % to about 40 wt % the total composition;
t5) from about 0.1 wt % to about 35 wt % the total composition;
t6) from about 0.1 wt % to about 30 wt % the total composition;
t7) from about 0.1 wt % to about 25 wt % the total composition;
t8) from about 0.1 wt % to about 20 wt % the total composition;
t9) from about 0.1 wt % to about 15 wt % the total composition;
t10) from about 0.2 wt % to about 15 wt % the total composition;
t11) from about 0.3 wt % to about 15 wt % the total composition;
t12) from about 0.4 wt % to about 15 wt % the total composition;
t13) from about 0.5 wt % to about 15 wt % the total composition;
t14) from about 0.6 wt % to about 15 wt % the total composition;
t15) from about 0.7 wt % to about 15 wt % the total composition;
t16) from about 0.8 wt % to about 15 wt % the total composition;
t17) from about 0.9 wt % to about 15 wt % the total composition;
t18) from about 1 wt % to about 15 wt % the total composition;
t19) from about 2 wt % to about 15 wt % the total composition;
t20) from about 3 wt % to about 15 wt % the total composition;
t21) from about 4 wt % to about 15 wt % the total composition;

t22) from about 5 wt % to about 15 wt % the total composition;
t23) from about 6 wt % to about 15 wt % the total composition;
t24) from about 7 wt % to about 15 wt % the total composition;
t25) from about 8 wt % to about 15 wt % the total composition;
t26) from about 9 wt % to about 15 wt % the total composition;
t27) from about 10 wt % to about 15 wt % the total composition;
t28) from about 0.5 wt % to about 10 wt % the total composition;
t29) from about 1 wt % to about 10 wt % the total composition;
t30) from about 2 wt % to about 10 wt % the total composition;
t31) from about 3 wt % to about 10 wt % the total composition;
t32) from about 4 wt % to about 10 wt % the total composition;
t33) from about 5 wt % to about 10 wt % the total composition;
t34) from about 5 wt % to about 9 wt % the total composition;
t35) from about 5 wt % to about 8 wt % the total composition;
t36) from about 5 wt % to about 7 wt % the total composition;
t37) from about 5 wt % to about 6 wt % the total composition;
t38) from about 7 wt % to about 8 wt % the total composition;
t39) from about 6 wt % to about 9 wt % the total composition;
t40) from about 6 wt % to about 8 wt % the total composition;
t41) from about 5 wt % to about 15 wt % the total composition;
t42) from about 5 wt % to about 20 wt % the total composition;
t43) from about 2 wt % to about 4 wt % the total composition;
t44) from about 1 wt % to about 5 wt % the total composition;
t45) from about 1 wt % to about 8 wt % the total composition; or
t46) from about 1 wt % to about 10 wt % the total composition.

The foregoing percentages, concentrations, and ratios are presented by example only and are not intended to be exhaustive or to limit the disclosure to the precise percentages, concentrations, and ratios disclosed. It should be appreciated that each value that falls within a disclosed range is disclosed as if it were individually disclosed as set forth herein. For example, a range indicating a weight percent from about 8% to about 14% additionally includes ranges beginning or ending with all values within that range, including for example a range beginning at 8.1%, 8.2%, 8.3%, 9%, 10%, 11%, 12%, and so forth.

Also, according to one or more non-limiting embodiments of the disclosure, any of the concentrations for ingredients for a combination of the ingredients (a) thru (jj), for example, as listed above, may indicate the concentration for other ingredients listed above.

Example 1 is a composition. The composition includes one or more of a first group consisting of milk thistle, ashwagandha, green tea, bacopa monnieri, and turmeric. The composition includes one or more of a second group consisting of acetyl-L-carnitine, quercetin, lipoic acid, coenzyme Q10, cysteine, and grape. The composition includes one or more of a third group consisting of wasabi, theacrine, copper, niacin, cysteine, and olive extract.

Example 2 is a composition as in Example 1, wherein one or more of: the milk thistle extract is screened milk thistle extract; the ashwagandha extract is screened ashwagandha extract; the green tea extract is screened green tea extract; the bacopa monnieri extract is screened bacopa monnieri extract; or the turmeric extract is screened turmeric extract.

Example 3 is a composition as in any of Examples 1-2, wherein one or more of: the acetyl-L-carnitine is acetyl-L-carnitine; the quercetin has greater than or equal to 90% purity; the lipoic acid has greater than or equal to 98% purity; the coenzyme Q10 has greater than or equal to 95% purity; or the grape extract is screened grape.

Example 4 is a composition as in any of Examples 1-3, wherein one or more of: the wasabi powder is wasabi japonica; the copper and the cuprous niacin form a copper-niacin complex comprising from 50 wt % to 80 wt % cuprous niacin and comprising from 10 wt % to 30 wt % copper; or the olive leaf extract comprises from 5 wt % to 20 wt % hydroxytyrosol.

Example 5 is a composition as in any of Examples 1-4, wherein: the one or more of the first group is present in the composition in an effective amount for increasing activation of an Nrf2 pathway in a body; the one or more of the second group is present in the composition in an effective amount for increasing activation of an NRF1 pathway in the body; and the one or more of the third group is present in the composition in an effective amount for increasing activation of an NAD pathway in the body.

Example 6 is a composition as in any of Examples 1-5, wherein the one or more of the first group is present in the composition in an effective amount for increasing expression of each of an NQO1 gene in a body and a HMOX1 gene in the body.

Example 7 is a composition as in any of Examples 1-6, wherein the one or more of the second group is present in the composition in an effective amount for increasing expression of each of an Nrf1 gene in a body and an PCG1-alpha gene in the body.

Example 8 is a composition as in any of Examples 1-7, wherein the one or more of the third group is present in the composition in an effective amount for increasing expression of each of an NMNAT1 gene in a body and an NAMPT gene in the body.

Example 9 is a composition as in any of Examples 1-8, wherein the one or more of the first group is present in the composition in an effective amount for reducing oxidative stress and increasing detoxification in a body.

Example 10 is a composition as in any of Examples 1-9, wherein the composition comprises multiple doses to be provided to a user, wherein the first group comprises one or more doses, the second group comprises one or more doses, and the third group comprises one or more doses, wherein the doses for the first group, the second group, and the third group are independent of one another.

Example 11 is a composition. The composition includes an effective amount of one or more elements of an Nrf2 group for increasing activity of an Nrf2 pathway in a body, the Nrf2 group comprising milk thistle extract, ashwagandha extract, green tea extract, bacopa monnieri extract, and turmeric extract. The composition includes an effective amount of one or more elements of an NRF1 group for increasing activity of an NRF1 pathway in the body, the NRF1 group comprising acetyl-L-carnitine, quercetin, lipoic acid, and coenzyme Q10. The composition includes an effective amount of one or more elements of an NAD group for increasing activity of an NAD pathway in the body, the NAD group comprising wasabi powder, theacrine, copper, cuprous niacin, and olive leaf extract.

Example 12 is a composition as in Example 11, wherein: the milk thistle extract is screened milk thistle extract 80 wt % silymarin; the ashwagandha extract is screened ashwagandha extract 0.35% withaferin A; the green tea extract is screened green tea extract 45% epigallocatechin gallate (EGCG); the bacopa monnieri extract is screened bacopa monnieri extract 45% bacosides; and the turmeric extract is screened turmeric extract.

Example 13 is a composition as in any of Examples 11-12, wherein: the acetyl-L-carnitine is acetyl-L-carnitine with greater than or equal to 95% purity; the quercetin has greater than or equal to 90% purity; the lipoic acid has greater than or equal to 98% purity; the coenzyme Q10 has greater than or equal to 95% purity; and the grape extract is screened grape.

Example 14 is a composition as in any of Examples 11-13, wherein: the wasabi powder is wasabi japonica; the copper and the cuprous niacin form a copper-niacin complex comprising from 50 wt % to 80 wt % cuprous niacin and comprising from 10 wt % to 30 wt % copper; and the olive leaf extract comprises from 5 wt % to 20 wt % hydroxytyrosol.

Example 15 is a composition as in any of Examples 11-14, wherein the effective amount of the one or more elements of the Nrf2 group is an effective amount for increasing expression of each of an NQO1 gene in the body and a HMOX1 gene in the body.

Example 16 is a composition as in any of Examples 11-15, wherein the effective amount of the one or more elements of the NRF1 group is an effective amount for increasing expression of each of an Nrf1 gene in the body and an PCG1-alpha gene in the body.

Example 17 is a composition as in any of Examples 11-16, wherein the effective amount of the one or more elements of the NAD group is an effective amount for increasing expression of each of an NMNAT1 gene in the body and an NAMPT gene in the body.

Example 18 is a composition as in any of Examples 11-17, wherein the composition comprises one or more independent compositions each encapsulated in a capsule.

Example 19 is a composition as in any of Examples 11-18, wherein the composition is prepared for one or more of: oral administration as a capsule; oral administration as a tablet; intravenous administration; or intramuscular administration.

Example 20 is a method for slowing the effects of aging in a user by improving overall stress response. The method includes providing a composition to the user. The composition includes one or more of a first group consisting of milk thistle extract, ashwagandha extract, green tea extract, bacopa monnieri extract, and turmeric extract. The composition includes one or more of a second group consisting of acetyl-L-carnitine, quercetin, lipoic acid, coenzyme Q10, and grape extract. The composition includes one or more of a third group consisting of wasabi powder, theacrine, copper, cuprous niacin, and olive leaf extract.

Example 21 is a method as in Example 20, wherein one or more of: the milk thistle extract is screened milk thistle extract 80 wt % silymarin; the ashwagandha extract is screened ashwagandha extract 0.35% withaferin A; the green tea extract is screened green tea extract 45% epigallocatechin gallate (EGCG); the bacopa monnieri extract is screened bacopa monnieri extract 45% bacosides; or the turmeric extract is screened turmeric extract.

Example 22 is a method as in any of Examples 20-21, wherein one or more of: the acetyl-L-carnitine is acetyl-L-carnitine with greater than or equal to 95% purity; the quercetin has greater than or equal to 90% purity; the lipoic acid has greater than or equal to 98% purity; the coenzyme Q10 has greater than or equal to 95% purity; or the grape extract is screened grape.

Example 23 is a method as in any of Examples 20-22, wherein one or more of: the wasabi powder is wasabi japonica; the copper and the cuprous niacin form a copper-niacin complex comprising from 50 wt % to 80 wt % cuprous niacin and comprising from 10 wt % to 30 wt % copper; or the olive leaf extract comprises from 5 wt % to 20 wt % hydroxytyrosol.

Example 24 is a method as in any of Examples 20-23, wherein: the one or more of the first group is present in the composition in an effective amount for increasing activation of an Nrf2 pathway in the user; the one or more of the second group is present in the composition in an effective amount for increasing activation of an NRF1 pathway in the user; and the one or more of the third group is present in the composition in an effective amount for increasing activation of an NAD pathway in the user.

Example 25 is a method as in any of Examples 20-24, wherein the one or more of the first group is present in the composition in an effective amount for increasing expression of each of an NQO1 gene in the user and an HMOX1 gene in the user.

Example 26 is a method as in any of Examples 20-25, wherein the one or more of the second group is present in the composition in an effective amount for increasing expression of each of an Nrf1 gene in the user and an PCG1-alpha gene in the user.

Example 27 is a method as in any of Examples 20-26, wherein the one or more of the third group is present in the composition in an effective amount for increasing expression of each of an NMNAT1 gene in the user and an NAMPT gene in the user.

Example 28 is a method as in any of Examples 20-27, wherein providing the composition to the user comprises providing multiple independent doses to the user, wherein the first group is provided in a first dose, the second group is provided in a second dose, and the third group is provided in a third dose.

Example 29 is a composition. The composition includes one or more of a first group comprising milk thistle extract, ashwagandha extract, green tea extract, bacopa monnieri extract, and turmeric extract. The composition includes one or more of a second group comprising acetyl-L-carnitine, quercetin, lipoic acid, coenzyme Q10, and grape extract. The composition includes one or more of a third group comprising wasabi powder, theacrine, copper, cuprous niacin, and olive leaf extract.

Example 30 is a composition as in Example 29, wherein one or more of: the milk thistle extract is screened milk thistle extract 80 wt % silymarin; the ashwagandha extract is screened ashwagandha extract 0.35% withaferin A; the green tea extract is screened green tea extract 45% epigallocatechin gallate (EGCG); the bacopa monnieri extract is screened bacopa monnieri extract 45% bacosides; or the turmeric extract is screened turmeric extract.

Example 31 is a composition as in any of Examples 29-30, wherein one or more of: the acetyl-L-carnitine is acetyl-L-carnitine with greater than or equal to 95% purity; the quercetin has greater than or equal to 90% purity; the lipoic acid has greater than or equal to 98% purity; the coenzyme Q10 has greater than or equal to 95% purity; or the grape extract is screened grape.

Example 32 is a composition as in any of Examples 29-31, wherein one or more of: the wasabi powder is wasabi japonica; the copper and the cuprous niacin form a copper-niacin complex comprising from 50 wt % to 80 wt % cuprous niacin and comprising from 10 wt % to 30 wt % copper; or the olive leaf extract comprises from 5 wt % to 20 wt % hydroxytyrosol.

Example 33 is a composition as in any of Examples 29-32 wherein: the one or more of the first group is present in the composition in an effective amount for increasing activation of an Nrf2 pathway in a body; the one or more of the second group is present in the composition in an effective amount for increasing activation of an NRF1 pathway in the body; and the one or more of the third group is present in the composition in an effective amount for increasing activation of an NAD pathway in the body.

Example 34 is a composition as in any of Examples 29-33, wherein the one or more of the first group is present in the composition in an effective amount for increasing expression of each of an NQO1 gene in a body and a HMOX1 gene in the body.

Example 35 is a composition as in any of Examples 29-34, wherein the one or more of the second group is present in the composition in an effective amount for increasing expression of each of an Nrf1 gene in a body and an PCG1-alpha gene in the body.

Example 36 is a composition as in any of Examples 29-35, wherein the one or more of the third group is present in the composition in an effective amount for increasing expression of each of an NMNAT1 gene in a body and an NAMPT gene in the body.

Example 37 is a composition as in any of Examples 29-36, wherein the one or more of the first group is present in the composition in an effective amount for reducing oxidative stress and increasing detoxification in a body.

Example 38 is a composition as in any of Examples 29-37, wherein the composition comprises multiple doses to be provided to a user, wherein the first group comprises one or more doses, the second group comprises one or more doses, and the third group comprises one or more doses, wherein the doses for the first group, the second group, and the third group are independent of one another.

Example 39 is a method for slowing the effects of aging in a user by improving stress response. The method includes providing a composition to the user. The composition includes one or more of a first group comprising milk thistle extract, ashwagandha extract, green tea extract, bacopa monnieri extract, and turmeric extract. The composition includes one or more of a second group comprising acetyl-L-carnitine, quercetin, lipoic acid, coenzyme Q10, and grape extract. The composition includes one or more of a third group comprising wasabi powder, theacrine, copper, cuprous niacin, and olive leaf extract.

Example 40 is a method as in Example 39, wherein one or more of: the milk thistle extract is screened milk thistle extract 80 wt % silymarin; the ashwagandha extract is screened ashwagandha extract 0.35% withaferin A; the green tea extract is screened green tea extract 45% epigallocatechin gallate (EGCG); the bacopa monnieri extract is screened bacopa monnieri extract 45% bacosides; or the turmeric extract is screened turmeric extract.

Example 41 is a method as in any of Examples 39-40, wherein one or more of: the acetyl-L-carnitine is acetyl-L-carnitine with greater than or equal to 95% purity; the quercetin has greater than or equal to 90% purity; the lipoic acid has greater than or equal to 98% purity; the coenzyme Q10 has greater than or equal to 95% purity; or the grape extract is screened grape.

Example 42 is a method as in any of Examples 39-41, wherein one or more of: the wasabi powder is wasabi japonica; the copper and the cuprous niacin form a copper-niacin complex comprising from 50 wt % to 80 wt % cuprous niacin and comprising from 10 wt % to 30 wt % copper; or the olive leaf extract comprises from 5 wt % to 20 wt % hydroxytyrosol.

Example 43 is a method as in any of Examples 39-42, wherein: the one or more of the first group is present in the composition in an effective amount for increasing activation of an Nrf2 pathway in the user; the one or more of the second group is present in the composition in an effective amount for increasing activation of an NRF1 pathway in the user; and the one or more of the third group is present in the composition in an effective amount for increasing activation of an NAD pathway in the user.

Example 44 is a method as in any of Examples 39-43, wherein the one or more of the first group is present in the composition in an effective amount for increasing expression of each of an NQO1 gene in the user and a HMOX1 gene in the user.

Example 45 is a method as in any of Examples 39-44, wherein the one or more of the second group is present in the composition in an effective amount for increasing expression of each of an Nrf1 gene in the user and an PCG1-alpha gene in the user.

Example 46 is a method as in any of Examples 39-45, wherein the one or more of the third group is present in the composition in an effective amount for increasing expression of each of an NMNAT1 gene in the user and an NAMPT gene in the user.

Example 47 is a method as in any of Examples 39-46, wherein providing the composition to the user comprises providing multiple independent doses to the user, wherein the first group is provided in a first dose, the second group is provided in a second dose, and the third group is provided in a third dose.

Example 48 is a composition as in any of Examples 1-47, wherein the first group comprises milk thistle, ashwagandha, green tea, bacopa monnieri, turmeric, calcium, lychee, black pepper, sulforaphane, isothiocyanates, cinnamon, ginger, stilbenes, blueberry, broccoli, thioctic acids, asparagus, rosemary, carnosol, carnosolic acid, luteolin, and *Sophora japonica*.

Example 49 is a composition as in any of Examples 1-48, wherein the second group comprises carnitine, acetyl-L-carnitine, quercetin, lipoic acid, lipoamide, coenzyme Q10, ubiquinone, ubiquinol, tetraphenylphosphonium, pyrroloquinoline quinone, grape, ginseng, onion, and magnesium.

Example 50 is a composition as in any of Examples 1-49, wherein the third group comprises wasabi, theacrine, copper, niacin, cuprous niacin, nicotinic acid, nicotinamide, nicotinamide riboside, ribose, nicotinamide mononucleotide, tryptophan, quinolinic acid, NAMN, NAAD, olive leaf, olive, olive leaf extract, resveratrol, rhodiola, caffeine, theobromine, paraxanthine, theophylline, xanthines, mango, vitamin B12, and myricetin.

Example 51 is a composition as in any of Examples 1-50, wherein the first group consists of milk thistle, ashwagandha, green tea, bacopa monnieri, turmeric, calcium, lychee, black pepper, sulforaphane, isothiocyanates, cinnamon, ginger, stilbenes, blueberry, broccoli, thioctic acids, asparagus, rosemary, carnosol, carnosolic acid, luteolin, and *Sophora japonica*.

Example 52 is a composition as in any of Examples 1-51, wherein the second group consists of carnitine, acetyl-L-carnitine, quercetin, lipoic acid, lipoamide, coenzyme Q10, ubiquinone, ubiquinol, tetraphenylphosphonium, pyrroloquinoline quinone, grape, ginseng, onion, and magnesium.

Example 53 is a composition as in any of Examples 1-52, wherein the third group consists of wasabi, theacrine, copper, niacin, cuprous niacin, nicotinic acid, nicotinamide, nicotinamide riboside, ribose, nicotinamide mononucleotide, tryptophan, quinolinic acid, NAMN, NAAD, olive leaf, olive, olive leaf extract, resveratrol, rhodiola, caffeine, theobromine, paraxanthine, theophylline, xanthines, mango, vitamin B12, and myricetin.

Example 54 is a method as in any of Examples 1-53. The method includes reducing oxidative stress in a body by increasing activation of an Nrf2 pathway in the body through use of the composition.

Example 55 is a method as in any of Examples 1-54. The method includes generating enzymes capable of neutralizing more than 1,000,000 free radicals in a body by increasing activation of an Nrf2 pathway in the body through use of the composition.

Example 56 is a method as in any of Examples 1-55. The method includes detoxifying genes in a body by increasing activation of an Nrf2 pathway in the body through use of the composition.

Example 57 is a method as in any of Examples 1-56. The method includes enhancing cellular health in a body by increasing activation of an NRF1 pathway in the body through use of the composition.

Example 58 is a method as in any of Examples 1-57. The method includes increasing a quantity of energy produced by cells in a body by increasing activation of an NRF1 pathway in the body through use of the composition.

Example 59 is a method as in any of Examples 1-58. The method includes increasing mental focus and concentration for a user by increasing activation of an NAD pathway in the user through use of the composition.

Example 60 is a method as in any of Examples 1-59. The method includes increasing mental energy and physical energy for a user by increasing activation of an NAD pathway in the user through use of the composition.

Example 61 is a method as in any of Examples 1-60. The method includes regulating cholesterol levels in a user by increasing activation of an NAD pathway in the user through use of the composition.

Example 62 is a method as in any of Examples 1-61. The method includes improving blood flow in a user by increasing activation of an NAD pathway in the user through use of the composition.

Example 63 is a method as in any of Examples 1-62. The method includes ameliorating symptoms of aging in a user by increasing activation of each of an Nrf2 pathway, an NRF1 pathway, and an NAD pathway in the user through use of the composition.

Example 64 is a method as in any of Examples 1-63. The method includes increasing activation of stress response processes in a user by increasing activation of each of an Nrf2 pathway, an NRF1 pathway, and an NAD pathway in the user through user of the composition.

Example 65 is a composition as in any of Examples 1-64. The composition includes one or more of a first group consisting of milk thistle extract, ashwagandha extract, green tea extract, bacopa monnieri extract, and turmeric extract. The composition includes one or more of a second group consisting of acetyl-L-carnitine, quercetin, lipoic acid, coenzyme Q10, and grape extract. The composition includes one or more of a third group consisting of wasabi powder, theacrine, copper, cuprous niacin, and olive extract.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A composition comprising therapeutically effective amounts of:
   one or more of a first group consisting of milk thistle, ashwagandha, green tea, bacopa monnieri, and turmeric;
   one or more of a second group consisting of acetyl-L-carnitine, quercetin, lipoic acid, coenzyme Q10, cysteine, and grape; and
   one or more of a third group consisting of wasabi, theacrine, copper, nicacin, cysteine, and olive extract.

2. The composition of claim 1, wherein one or more of:
   the milk thistle extract is screened milk thistle extract;
   the ashwagandha extract is screened ashwagandha extract,
   the green tea extract is screened green tea extract;
   the bacopa monnieri extract is screened bacopa monnieri extract, or
   the turmeric extract is screened turmeric extract.

3. The composition of claim 1, wherein one or more of:
   the quercetin has greater than or equal to 90% purity;
   the lipoic acid has greater than or equal to 98% purity
   the coenzyme Q10 has greater than or equal to 95% purity; or
   the grape extract is screened grape.

4. The composition of claim 1, wherein the composition comprises copper and niacin, and wherein the copper and the niacin form a copper-niacin complex comprising from 50 wt % to 80 wt % cuprous niacin and comprising from 10 wt % to 30 wt % copper.

5. The composition of claim 1, wherein the composition comprises olive leaf extract, and wherein the olive leaf extract comprises from 5 wt % to 20 wt % hydroxytyrosol.

6. The composition of claim 1, wherein the composition comprises an effective amount of the one or more of the first group for increasing activation of an Nrf2 pathway in a body.

7. The composition of claim 1, wherein the composition comprises an effective amount of the one or more of the second group for increasing activation of an NRF1 pathway in a body.

8. The composition of claim 1, wherein the composition comprises an effective amount of the one or more of the third group for increasing activation of an NAD pathway in a body.

9. The composition of claim 1, wherein the composition comprises each of the first group, and wherein the first group is present in the composition in an effective amount for increasing expression of each of an NQO1 gene in a body and a HMOX1 gene in the body.

10. The composition of claim 1, wherein the composition comprises each of second group, and wherein the second group is present in the composition in an effective amount for increasing expression of each of an Nrf1 gene in a body and a PCG1-alpha gene in the body.

11. The composition of claim 1, wherein the composition comprises each of the third group, and wherein the third group is present in the composition in an effective amount for increasing expression of each of an NMNAT1 gene in a body and an NAMPT gene in the body.

12. The composition of claim 1, wherein the composition comprises an effective amount of the one or more of the first group for reducing oxidative stress and increasing detoxification in a body.

13. The composition of claim 1, wherein the composition comprises multiple doses to be provided to a user, and wherein each of the first group, the second group, and the third group comprises an independent dose to be taken simultaneously or in succession by the user.

14. The composition of claim 1, wherein the first group is an Nrf2 group for increasing activity of an Nrf2 pathway in a body, and wherein the composition comprises:
   an effective amount of the milk thistle;
   an effective amount of the ashwagandha;
   an effective amount of the green tea;
   an effective amount of the bacopa monnieri; and
   an effective amount of the turmeric for increasing activity of the Nrf2 pathway in the body.

15. The composition of claim 14, wherein the composition comprises an effective amount of the first group for increasing expression of an NQO1 gene in the body and a HMOX1 gene in the body.

16. The composition of claim 1, wherein the second group is an NRF1 group for increasing activity of an NRF1 pathway in a body, and wherein the composition comprises:
   an effective amount of the acetyl-L-carnitine;
   an effective amount of the quercetin;
   an effective amount of the lipoic acid;
   an effective amount of the coenzyme Q10;
   an effective amount of the cysteine; and
   an effective amount of the grape for increasing activity of the NRF1 pathway in the body.

17. The composition of claim 16, wherein the composition comprises an effective amount of the second group for increasing expression of an Nrf1 gene in the body and a PCG1-alpha gene in the body.

18. The composition of claim 1, wherein the third group is an NAD group for increasing activity of an NAD pathway in the body, and wherein the composition comprises:
   an effective amount of the wasabi;
   an effective amount of the theacrine;
   an effective amount of the copper;
   an effective amount of the niacin;
   an effective amount of the cysteine; and
   an effective amount of the olive extract for increasing activity of the NAD pathway in the body.

19. The composition of claim 18, wherein the composition comprises an effective amount of the third group for increasing expression of an NMNAT1 gene in the body and an NAMPT gene in the body.

20. The composition of claim 1, wherein the composition comprises the milk thistle, and wherein the milk thistle is screened milk thistle extract 80 wt % silymarin.

21. The composition of claim 1, wherein the composition comprises the green tea, and wherein the green tea is screened green tea extract 45% epigallocatechin gallate (EGCG).

22. The composition of claim 1, wherein the composition comprises the turmeric, and wherein the turmeric is screened turmeric extract.

23. The composition of claim 1, wherein the composition comprise one or more independent compositions each encapsulated in a capsule.

24. The composition of claim 23, wherein the composition comprises three or more independent capsules comprising a first capsule comprising the one or more of the first group, a second capsule comprising the one or more of the second group, and a third capsule comprising the one or more of the third group.

25. The composition of claim 1, wherein the composition is prepared for oral administration as a tablet.

26. The composition of claim 1, wherein the composition is prepared for intravenous administration.

27. The composition of claim 1, wherein the composition is prepared for intramuscular administration.

28. A method for slowing the effects of aging in a user by improving stress response, the method comprising:
   providing therapeutically effective amounts of a composition to the user, wherein the composition comprises:
      one or more of a first group consisting of milk thistle, ashwagandha, green tea, bacopa monnieri, and turmeric;
      one or more of a second group consisting of acetyl-L-carnitine, quercetin, lipoic acid, coenzyme Q10, cysteine, and grape; and
      one or more of a third group consisting of wasabi, theacrine, copper, nicacin, cysteine, and olive extract.

29. The method of claim 28, wherein one or more of:
   the composition comprises each of the first group, and wherein the first group is present in the composition in an effective amount for increasing expression of each of an NQO1 gene in a body and a HMOX1 gene in the body;
   the composition comprises each of second group, and wherein the second group is present in the composition in an effective amount for increasing expression of each of an Nrf1 gene in a body and a PCG1-alpha gene in the body; or
   the composition comprises each of the third group, and wherein the third group is present in the composition in an effective amount for increasing expression of each of an NMNAT1 gene in a body and an NAMPT gene in the body.

30. A composition comprising:
   an effective amount of a first group for increasing expression of each of an NQO1 gene in a body and a HMOX1 gene in the body, wherein the first group comprises milk thistle, ashwagandha, green tea, bacopa monnieri, and turmeric;
   an effective amount of a second group for increasing expression of an Nrf1 gene in the body and a PCG1-alpha gene in the body, wherein the second group comprises acetyl-L-carnitine, quercetin, lipoic acid, coenzyme Q10, cysteine, and grape leaf extract; and an effective amount of a third group for increasing expression of an NMNAT1 gene in the body and an NAMPT gene in the body, wherein the third group comprises wasabi, theacrine, copper niacin, cysteine, and olive leaf extract.

* * * * *